(12) United States Patent
Miyachi

(10) Patent No.: US 9,538,988 B2
(45) Date of Patent: Jan. 10, 2017

(54) ULTRASOUND DIAGNOSTIC APPARATUS AND METHOD OF PRODUCING ULTRASOUND IMAGE

(71) Applicant: FUJIFILM Corporation, Tokyo (JP)

(72) Inventor: Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 211 days.

(21) Appl. No.: 14/465,014

(22) Filed: Aug. 21, 2014

(65) Prior Publication Data
US 2015/0080729 A1    Mar. 19, 2015

(30) Foreign Application Priority Data

Sep. 13, 2013 (JP) ................. 2013-190412

(51) Int. Cl.
*A61B 8/14* (2006.01)
*A61B 8/08* (2006.01)

(52) U.S. Cl.
CPC ........... *A61B 8/5207* (2013.01); *A61B 8/0858* (2013.01); *A61B 8/0891* (2013.01); *A61B 8/485* (2013.01)

(58) Field of Classification Search
CPC ..... A61B 8/0858; A61B 8/0891; A61B 8/485; A61B 8/5207
See application file for complete search history.

(56) References Cited

U.S. PATENT DOCUMENTS

2012/0310090 A1* 12/2012 Miyachi ............... A61B 8/0858
                                                        600/440

FOREIGN PATENT DOCUMENTS

JP        2008-168016 A    7/2008
WO    WO 2011/099102 A1    8/2011

OTHER PUBLICATIONS

Japanese Office Action, dated Aug. 4, 2015, for Japanese Application No. 2013-190412, with a partial English translation.
Gustavsson et al., "A Dynamic Programming Procedure for Automated Ultrasonic Measurement of the Carotid Artery", 1994, in Proc IEEE Computers in Cardiology, pp. 297-300.
Extended European Search Report, dated Feb. 13, 2015, for European Application No. 14181513.4.

* cited by examiner

*Primary Examiner* — Mark Remaly
(74) *Attorney, Agent, or Firm* — Birch, Stewart, Kolasch & Birch, LLP

(57) ABSTRACT

An ultrasound diagnostic apparatus and a method of producing an ultrasound image capable of accurately determining the boundary of an intima-media complex in an ultrasound image and measuring an intima-media thickness with high precision are provided. A candidate vascular wall boundary point determiner determines one or more candidate vascular wall boundary points based on a sound ray signal extending in a scanning direction in an ultrasound image. A boundary determiner determines a vascular wall boundary point from among the candidate vascular wall boundary points based on a third evaluation value and determines a vascular wall boundary, the third evaluation value being calculated based on a first evaluation value representing accuracy of each of the determined candidate vascular wall boundary points as a vascular wall boundary point and a second evaluation value representing similarity between the sound ray signal and the adjacent sound ray signal.

20 Claims, 14 Drawing Sheets

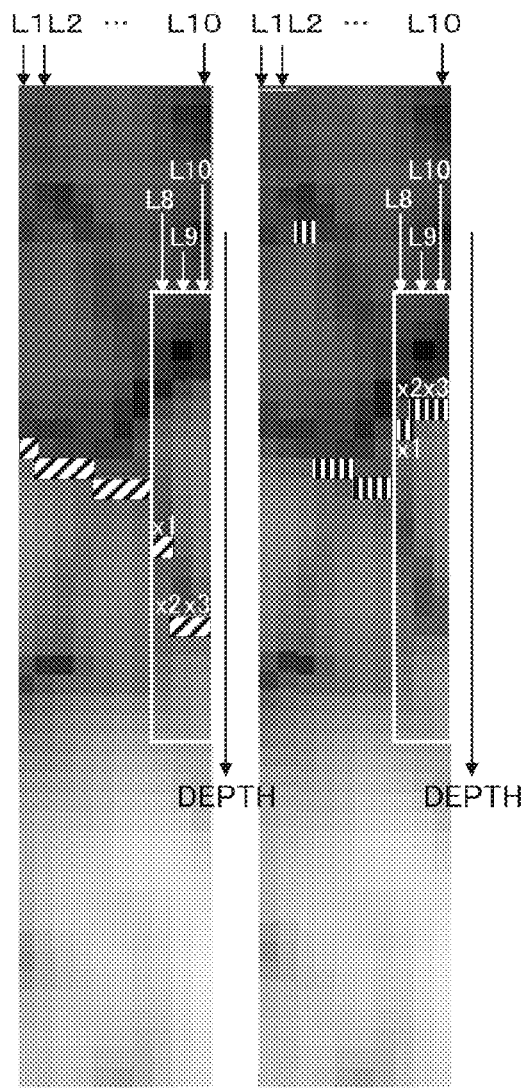
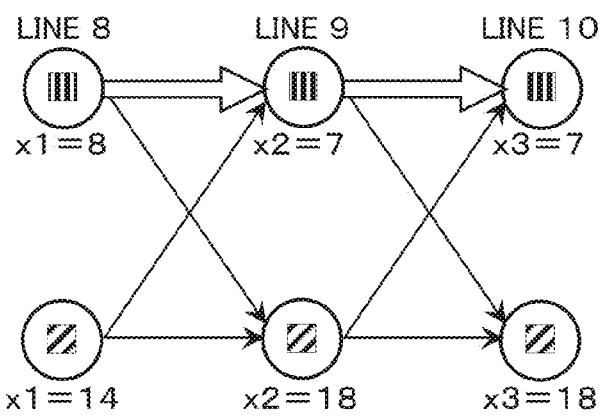

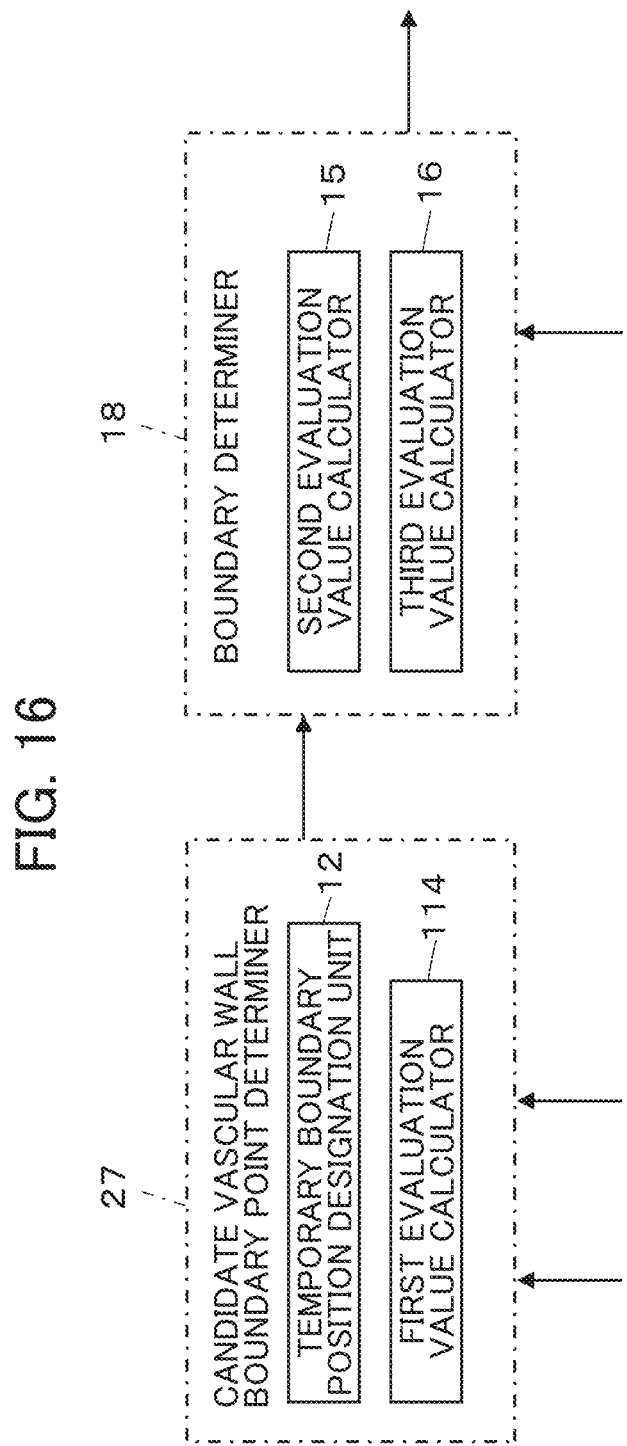

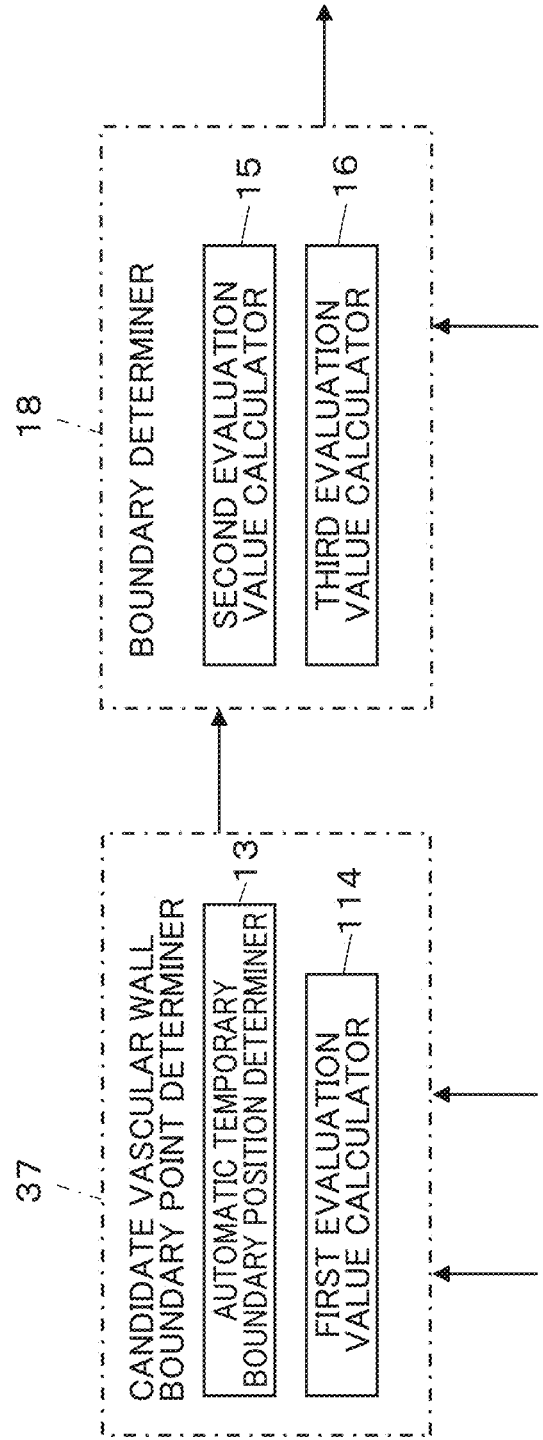

ULTRASOUND DIAGNOSTIC APPARATUS AND METHOD OF PRODUCING ULTRASOUND IMAGE

CROSS-REFERENCE TO RELATED APPLICATIONS

The present application claims priority under 35 U.S.C. §119 to Japanese Patent Application No. 2013-190412, filed on Sep. 13, 2013. Each of the above application(s) is hereby expressly incorporated by reference, in its entirety, into the present application.

BACKGROUND OF THE INVENTION

The present invention relates to an ultrasound diagnostic apparatus and a method of producing an ultrasound image, and in particular, to an ultrasound diagnostic apparatus and a method of producing an ultrasound image for measuring an intima-media thickness of a blood vessel.

An ultrasound diagnostic apparatus which carries out ultrasound diagnosis using an ultrasound image has hitherto been put into practical use in the field of medicine. In general, this type of ultrasound diagnostic apparatus has an ultrasound probe embedded with a transducer array, and a diagnostic apparatus body connected to the ultrasound probe. The ultrasound diagnostic apparatus transmits an ultrasonic wave from the ultrasound probe toward a subject, receives an ultrasonic echo from the subject by the ultrasound probe, and electrically processes the reception signal by the diagnostic apparatus body to produce an ultrasound image.

In the ultrasound diagnostic apparatus, various kinds of information which represent the state of a disease can be obtained based on the reception signal obtained by receiving the ultrasonic echo from the subject. For example, in order to obtain information regarding a circulatory system disease, such as arteriosclerosis or cerebral infarction, transmission and reception of an ultrasonic wave is carried out with respect to a blood vessel, and the intima-media thickness (IMT) or the like of a vascular wall is calculated based on the obtained reception signal. The value of the intima-media thickness changes along with the progress of arteriosclerosis, and the state of the circulatory system disease can be estimated by monitoring the value.

However, the vascular wall has a small thickness and further, noise is mixed in the reception signal due to the influence of a pulsation accompanying heartbeat, or the like, and therefore, it is difficult to accurately calculate the intima-media thickness of the vascular wall in the ultrasound image.

Accordingly, as a technique which accurately measures the intima-media thickness of a vascular wall in an ultrasound image, for example, as disclosed in JP 2008-168016 A (Patent Document 1), an ultrasound diagnostic apparatus which detects the boundary of an intima-media complex (vascular wall) based on the slope and the amount of change in the intensity distribution of sound ray signals to calculate an intima-media thickness has been suggested.

T. Gustavsson, Q. Liang, I. Wendelhag, and J. Wikistrand, "A dynamic programming procedure for automated ultrasonic measurement of the carotid artery," in Proc IEEE Computers Cardiology 1994, pp. 297-300 (Non-Patent Document 1) discloses a method which detects the boundary position of an IMT using a dynamic programming method based on an evaluation function including the intensity of a sound ray signal and the difference in the boundary position between adjacent sound rays.

WO 2011/099102 A1 (Patent Document 2) discloses an ultrasound diagnostic apparatus including a pattern similarity calculating unit which calculates pattern similarity based on a template representing a reference pattern of a vascular wall prepared in advance, and a boundary continuity calculating unit which calculates boundary continuity based on the difference in intensity value among a plurality of adjacent sound ray signals. In the ultrasound diagnostic apparatus, a boundary portion is determined based on a boundary evaluation value.

In the ultrasound diagnostic apparatus disclosed in Patent Document 1, a threshold value in evaluating the amount of change in luminance between the sound ray signals is set, and when the boundary of the intima-media complex is not detected, the threshold value is gradually decreased and the search range is gradually narrowed down, thereby distinguishing between the intima-media complex and noise and measuring the intima-media thickness of the blood vessel.

However, in the ultrasound diagnostic apparatus of Patent Document 1, when some of the sound ray signals drops out and the intensity thereof is degraded significantly, there is a high possibility that a vascular posterior wall intima-lumen boundary is erroneously detected as a lumen side, and it is not possible to measure the intima-media thickness with high precision.

In addition, in Non-Patent Document 1, since continuity of adjacent sound rays depends on only difference information of the boundary position, there is a problem in that a point where a signal is weak represents the same position as an adjacent signal ray, and a region, such as plaque, where intensity largely changes cannot be tracked.

Moreover, in Patent Document 2, continuity of adjacent sound rays is determined based on the difference in intensity value, and accordingly, as in Non-Patent Document 1, there is a problem in that the ultrasound diagnostic apparatus is susceptible to a portion where there is change from a point at which a signal is strong to a point where a signal is weak, and in particular, is susceptible to a case where noise produced in a vascular posterior wall and noise produced in a vascular lumen are close to each other in position (fogging) and strong. In addition, pattern matching using the reference pattern can track a normal region, but is susceptible to hyperplasia, plaque, or the like.

SUMMARY OF THE INVENTION

The invention has been accomplished in order to solve the aforementioned problems in the prior art, and an object of the invention is to provide an ultrasound diagnostic apparatus and a method of producing an ultrasound image capable of accurately determining the boundary of an intima-media complex in each sound ray and measuring an intima-media thickness with high precision.

In order to solve the aforementioned problems, the invention provides an ultrasound diagnostic apparatus which performs transmission and reception of an ultrasonic beam from an ultrasound probe toward a blood vessel in a subject and produces an ultrasound image based on a sound ray signal obtained by processing a reception signal output from the ultrasound probe, the ultrasound diagnostic apparatus comprising:

a candidate vascular wall boundary point determiner which determines candidate vascular wall boundary points based on the sound ray signal;

a first evaluation value calculator which calculates a first evaluation value representing accuracy of each of the determined candidate vascular wall boundary points as a vascular wall boundary point;

a second evaluation value calculator which, by means of a sound ray signal in a predetermined depth range including the determined candidate vascular wall boundary points and a sound ray signal adjacent to the sound ray signal, calculates a second evaluation value representing similarity between the sound ray signal and the adjacent sound ray signal;

a third evaluation value calculator which calculates a third evaluation value for determining the vascular wall boundary point from among the candidate vascular wall boundary points based on the first evaluation value and the second evaluation value; and a boundary determiner which determines the vascular wall boundary point based on the third evaluation value and determines a vascular wall boundary based on the determined vascular wall boundary point.

It is preferable that the candidate vascular wall boundary point determiner includes a temporary boundary position designation unit configured to designate a temporary lumen-intima boundary position and a temporary media-adventitia boundary position for the sound ray signal, and determines a search depth range of the candidate vascular wall boundary points based on the temporary lumen-intima boundary position and the temporary media-adventitia boundary position designated by the temporary boundary position designation unit.

It is preferable that the candidate vascular wall boundary point determiner includes an automatic temporary boundary position determiner which automatically determines a temporary lumen-intima boundary position and a temporary media-adventitia boundary position for the sound ray signal, determines the temporary lumen-intima boundary position and the temporary media-adventitia boundary position based on at least one of the intensity and the amount of change of the sound ray signal, and determines a search depth range of the candidate vascular wall boundary points based on the temporary lumen-intima boundary position and the temporary media-adventitia boundary position.

It is preferable that the candidate vascular wall boundary point determiner further calculates a maximum point giving the maximum value of the intensity of the sound ray signal within the search depth range, calculates a shallow portion local maximum point having a local maximum value equal to or greater than a first threshold value at a place shallower than the maximum point and separated from the maximum point more than half the wave train length of a transmission wave at the time of the transmission and reception of the ultrasonic beam within the search depth range, calculates a first point of interest having intensity of about a second threshold value at a place shallower than the maximum point and within a length of half the wave train length of the transmission wave from the maximum point of the intensity within the search depth range, calculates a second point of interest having intensity of about a third threshold value at a place shallower than the shallow portion local maximum point and within a length of half the wave train length of the transmission wave from the shallow portion local maximum point within the search depth range, and determines the first point of interest and the second point of interest as the candidate vascular wall boundary points.

It is preferable that the first evaluation value calculator calculates the first evaluation value based on the distance between the maximum point of the intensity within the search depth range of the sound ray signal and each of the candidate vascular wall boundary points.

It is preferable that the first evaluation value calculator calculates the first evaluation value based on a first evaluation function $C1(b_i(j))$ which takes a maximum value at an intensity position of 10 to 80% of the maximum value of the intensity within the search depth range of the sound ray signal, attenuates as a distance therefrom becomes far and becomes zero at a place separated therefrom by about the wave train length of the transmission wave, and which has a candidate vascular wall boundary position (depth) $b_i(j)$ (where j represents a depth direction position of a candidate vascular wall boundary point) corresponding to the boundary of an intima-media complex of a sound ray $L_i$ (where i represents the position of a sound ray in a scan direction).

It is preferable that the candidate vascular wall boundary point determiner determines a plurality of candidate vascular wall boundary points in a descending order of intensity from a maximum point giving the maximum value of the intensity in each sound ray signal within the search depth range, and the first evaluation value calculator calculates, in each of a plurality of the points of interest, at least one shallow portion local maximum point having a local maximum value equal to or greater than a predetermined threshold value at a place shallower than the point of interest and separated from the point of interest more than half the wave train length of the transmission wave at the time of the transmission and reception of the ultrasonic beam within the search depth range, and calculates the first evaluation value based on a first evaluation function which takes a maximum value in at least one shallow portion local maximum point and becomes zero at a place separated therefrom more than the wave train length of the transmission wave.

It is preferable that when there are a plurality of first evaluation values, the first evaluation value calculator calculates the maximum value of the first evaluation values as the first evaluation value in each of the candidate vascular wall boundary points.

Moreover, the invention provides an ultrasound diagnostic apparatus which performs transmission and reception of an ultrasonic beam from an ultrasound probe toward a blood vessel in a subject and produces an ultrasound image based on a sound ray signal obtained by processing a reception signal output from the ultrasound probe, the ultrasound diagnostic apparatus comprising:

a first evaluation value calculator which calculates a first evaluation value representing accuracy as a vascular wall boundary of the sound ray signal;

a candidate vascular wall boundary point determiner which determines candidate vascular wall boundary points based on the first evaluation value;

a second evaluation value calculator which, by means of a sound ray signal in a predetermined depth range including the determined candidate vascular wall boundary points and a sound ray signal adjacent to the sound ray signal, calculates a second evaluation value representing similarly between the sound ray signal and the adjacent sound ray signal;

a third evaluation value calculator which calculates a third evaluation value for determining the vascular wall boundary point from among the candidate vascular wall boundary points based on the first evaluation value and the second evaluation value; and a boundary determiner which determines the vascular wall boundary point based on the third evaluation value and determines a vascular wall boundary based on the determined vascular wall boundary point.

It is preferable that the candidate vascular wall boundary point determiner includes a temporary boundary position designation unit configured to designate a temporary lumen-intima boundary position and a temporary media-adventitia boundary position for the sound ray signal, and determines a search depth range of the candidate vascular wall boundary points based on the temporary lumen-intima boundary position and the temporary media-adventitia boundary position designated by the temporary boundary position designation unit.

It is preferable that the candidate vascular wall boundary point determiner includes an automatic temporary boundary position determiner which automatically determines a temporary lumen-intima boundary position and a temporary media-adventitia boundary position for the sound ray signal, determines the temporary lumen-intima boundary position and the temporary media-adventitia boundary position based on at least one of the intensity and the amount of change of the sound ray signal, and determines a search depth range in the candidate vascular wall boundary points based on the temporary lumen-intima boundary position and the temporary media-adventitia boundary position.

It is preferable that the first evaluation value calculator calculates a plurality of points of interest in a descending order of intensity from a maximum point giving the maximum value of the intensity in each sound ray signal within the search depth range, calculates, in each of a plurality of the points of interest, at least one shallow portion local maximum point having a local maximum value equal to or greater than a predetermined threshold value at a place shallower than the point of interest and separated from the point of interest more than half the wave train length of the transmission wave at the time of the transmission and reception of the ultrasonic beam within the search depth range, and calculates the first evaluation value based on a first evaluation function which takes a maximum value in at least one shallow portion local maximum point and becomes zero at a place separated therefrom more than the wave train length of the transmission wave.

It is preferable that when there are a plurality of first evaluation values, the first evaluation value calculator calculates the maximum value of the first evaluation values as the first evaluation value.

It is preferable that the candidate vascular wall boundary point determiner determines, as the candidate vascular wall boundary points, each point of the sound ray signal in which the first evaluation value is equal to or greater than a predetermined value, or the vicinity of each point of the sound ray signal in which the first evaluation value is equal to or greater than a predetermined value.

It is preferable that the first evaluation value calculator sets a first evaluation function by respectively multiplying the intensity of the sound ray signal and the amount of change in intensity of the sound ray signal by a predetermined coefficient and adding the multiplication result, and the candidate vascular wall boundary point determiner determines, as the candidate vascular wall boundary point, a point in which the first evaluation value calculated by the first evaluation function is equal to or greater than a predetermined value.

It is preferable that the first evaluation value calculator sets a first evaluation function by respectively multiplying the amounts of change in intensity of the sound ray signal by a predetermined coefficient and adding the multiplication result, and the candidate vascular wall boundary point determiner determines, as the candidate vascular wall boundary point, a point in which the first evaluation value calculated by the first evaluation function is equal to or greater than a predetermined value.

It is preferable that the second evaluation value is calculated on the basis of a second evaluation function which represents the deviation of the intensity distribution between one sound ray signal and another sound ray signal different from the sound ray signal.

It is preferable that the second evaluation value is calculated by the following second evaluation function $C2(b_{i-1}(j), b_i(j'))$ using sound ray signals of a plurality of points above and below a candidate vascular wall boundary point including the candidate vascular wall boundary point in a depth direction and sound ray signals adjacent to the sound ray signals.

[Equation 1]
$$C2(b_{i-1}(j), b_i(j')) = \frac{\sum_{k=0}^{WL-1}\left\{f[i-1, j+k] - \left(\sum_{k=0}^{WL-1} f[i-1, j+k]/WL\right)\right\} \left\{f[i, j'+k] - \left(\sum_{k=0}^{WL-1} f[i, j'+k]/WL\right)\right\}}{\sqrt{\sum_{k=0}^{WL-1}\left\{f[i-1, j+k] - \left(\sum_{k=0}^{WL-1} f[i-1, j+k]/WL\right)\right\}^2} \sqrt{\sum_{k=0}^{WL-1}\left\{f[i, j'+k] - \left(\sum_{k=0}^{WL-1} f[i, j'+k]/WL\right)\right\}^2}};$$

$b_i$: a candidate vascular wall boundary position (depth) corresponding to the boundary of an intima-media complex of a sound ray $L_i$, i: the position of a sound ray in a scan direction, j, j': the depth direction positions of the candidate vascular wall boundary points, k: a search depth range, WL: a depth range in which similarity calculation (correlation calculation) is performed (the number of sampling points corresponding to about a wave train length of a transmission wave).

It is preferable that the second evaluation value is calculated based on a correlation coefficient, a normalized cross-correlation coefficient, the sum of the squares of differences in intensity, or the sum of the absolute values of difference in intensity between sound ray signals of a plurality of points above and below the candidate vascular wall boundary point including the candidate vascular wall boundary point in a depth direction and sound ray signals adjacent to the sound ray signals.

It is preferable that the third evaluation value is calculated by the following third evaluation function $C_{sum}$ based on the first evaluation value and the second evaluation value.

$$C_{sum} = \sum_{i=1}^{N} C(b_{i-1}(j), b_i(j'));$$ [Equation 2]

$C(b_{i-1}(j),b_i(j'))=W1C1(b_i(j'))+W2C2(b_{i-1}(j),b_i(j'));$

W1, W2: a weighting function;
$b_{i-1}(j)$: a candidate vascular wall boundary position (depth) corresponding to the boundary of an intima-media complex of a sound ray $L_{i-1}$; and
$b_i(j')$: a candidate vascular wall boundary position (depth) corresponding to a boundary of an intima-media complex of a sound ray $L_i$.

It is preferable that the calculation of the third evaluation value in the boundary determiner is performed using a dynamic programming method.

It is preferable that the boundary determiner sets a combination of candidate vascular wall boundary points, in which the third evaluation value is maximized, as the vascular wall boundary.

It is preferable that the vascular wall boundary is a lumen-intima boundary or a media-adventitia boundary.

It is preferable that the ultrasound diagnostic apparatus further includes an IMT calculator which calculates an intima-media thickness based on the vascular wall boundary determined by the boundary determiner.

In addition, the invention provides a method of producing an ultrasound image which performs transmission and reception of an ultrasonic beam from an ultrasound probe toward a blood vessel in a subject and produces an ultrasound image based on a sound ray signal obtained by processing a reception signal output from the ultrasound probe, the method comprising:

determining candidate vascular wall boundary points based on the sound ray signal;

calculating a first evaluation value representing accuracy of each of the determined candidate vascular wall boundary points as a vascular wall boundary point;

by means of a sound ray signal in a predetermined depth range including the determined candidate vascular wall boundary points and a sound ray signal adjacent to the sound ray signal, calculating a second evaluation value representing similarly between the sound ray signal and the adjacent sound ray signal;

calculating a third evaluation value for determining the vascular wall boundary point from among the candidate vascular wall boundary points based on the first evaluation value and the second evaluation value; and determining the vascular wall boundary point based on the third evaluation value and determining a vascular wall boundary based on the determined vascular wall boundary point.

Moreover, the invention provides a method of producing an ultrasound image which performs transmission and reception of an ultrasonic beam from an ultrasound probe toward a blood vessel in a subject and produces an ultrasound image based on a sound ray signal obtained by processing a reception signal output from the ultrasound probe, the method comprising:

calculating a first evaluation value representing accuracy as a vascular wall boundary of the sound ray signal;

determining candidate vascular wall boundary points based on the first evaluation value;

by means of a sound ray signal in a predetermined depth range including the determined candidate vascular wall boundary points and a sound ray signal adjacent to the sound ray signal, calculating a second evaluation value representing similarly between the sound ray signal and the adjacent sound ray signal;

calculating a third evaluation value for determining the vascular wall boundary point from among the candidate vascular wall boundary points based on the first evaluation value and the second evaluation value; and determining the vascular wall boundary point based on the third evaluation value and determining a vascular wall boundary based on the determined vascular wall boundary point.

According to the invention, it is possible to accurately determine the boundary of an intima-media complex in an ultrasound image and to measure an intima-media thickness based on the boundary with high precision.

BRIEF DESCRIPTION OF THE DRAWINGS

FIGS. 11A and 11B are explanatory views illustrating eighth to tenth lines (eighth to tenth sound rays) in which boundary candidates are roughly divided into two kinds.

FIG. 12 is an explanatory view illustrating a plurality of boundary candidates consisting of a plurality of combinations of candidate vascular wall boundary candidate points shown in FIGS. 11A and 11B.

FIG. 16 is a block diagram showing the partial configuration of a modification example of the ultrasound diagnostic apparatus according to Embodiment 1 of FIG. 1.

FIG. 17 is a block diagram showing the partial configuration of a modification example of the ultrasound diagnostic apparatus according to Embodiment 2 of FIG. 13.

DETAILED DESCRIPTION OF THE INVENTION

Hereinafter, embodiments of the invention will be described referring to the accompanying drawings.

Embodiment 1

Figure 1:
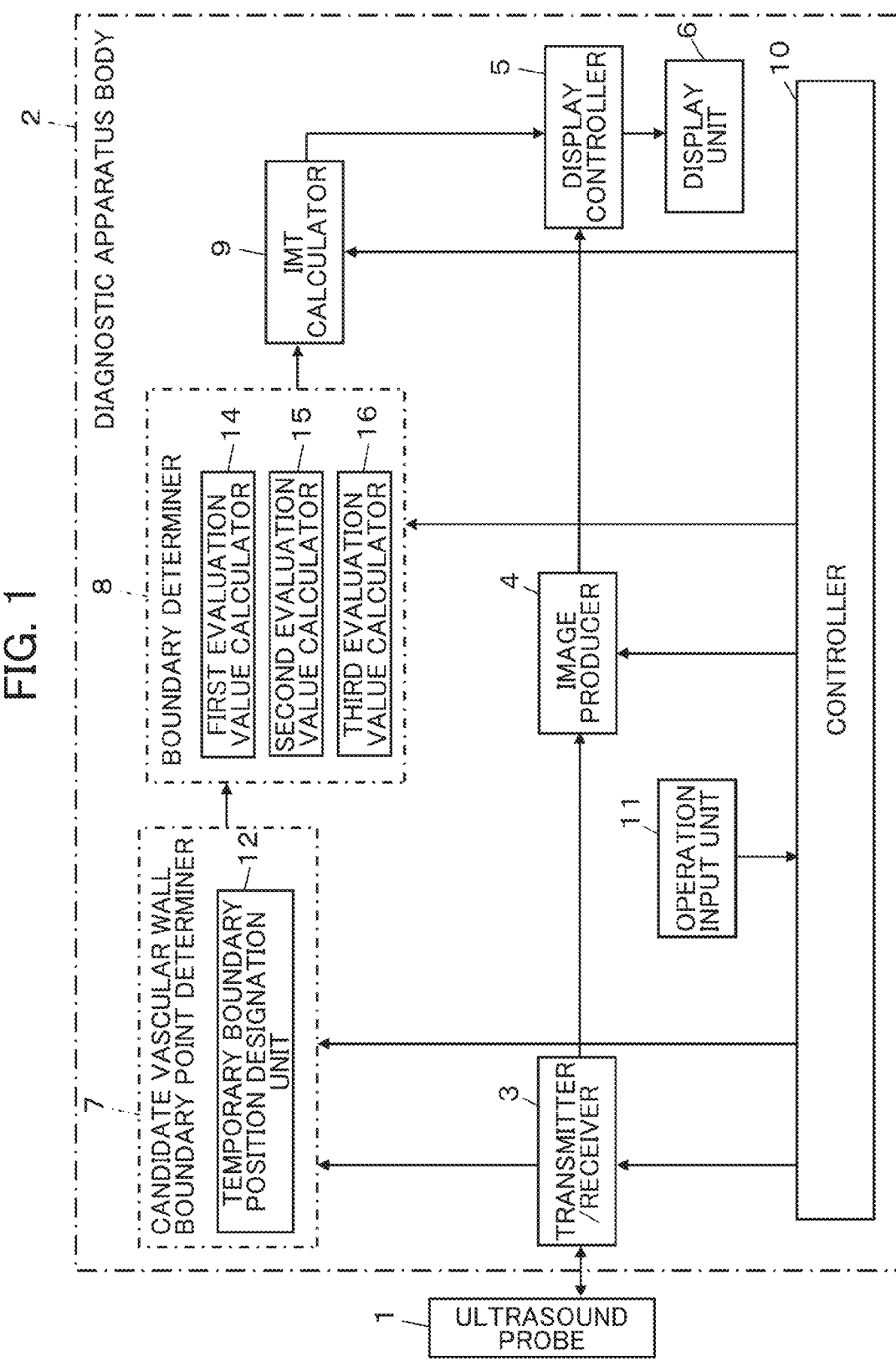
FIG. 1 is a block diagram showing the configuration of an ultrasound diagnostic apparatus according to Embodiment 1 of the invention.

FIG. 1 is a block diagram showing the configuration of an ultrasound diagnostic apparatus according to Embodiment 1 of the invention. The ultrasound diagnostic apparatus includes an ultrasound probe 1 which transmits and receives an ultrasonic wave, and a diagnostic apparatus body 2 connected to the ultrasound probe 1. The diagnostic apparatus body 2 has a function of producing an ultrasound image based on a reception signal acquired by transmitting and receiving an ultrasonic wave from the ultrasound probe 1 toward a blood vessel in a subject and detecting the boundary of an intima-media complex of the blood vessel in the ultrasound image to calculate an intima-media thickness.

The ultrasound probe 1 is, for example, a convex type, linear scan type, or sector scan type probe, which is used by causing it to come into contact with the body surface of the subject. The ultrasound probe 1 includes a plurality of ultrasound transducers arranged in a one-dimensional or two-dimensional manner. Each of these ultrasound transducers transmits an ultrasonic wave toward the blood vessel in the subject based on an actuation signal to be applied and receives an ultrasonic echo reflected by the blood vessel in the subject to output reception signal.

Each ultrasound transducer is constituted by a vibrator in which electrodes are formed at both ends of a piezoelectric substance composed of, for example, piezoelectric ceramic represented by PZT (Pb (lead) zirconate titanate), a polymer piezoelectric element represented by PVDF (polyvinylidene difluoride), and the like. If a pulsed or continuous-wave voltage is applied to the electrodes of the vibrator, the piezoelectric substance expands and contracts. With the expansion and contraction, pulsed or continuous-wave ultrasonic waves are produced from the respective vibrators, and an ultrasonic beam is produced by synthesizing these ultrasonic waves. When receiving the propagating ultrasonic waves, the respective vibrators expand and contract to produce electrical signals. These electrical signals are output as the reception signals of the ultrasonic waves.

The diagnostic apparatus body 2 has a transmitter/receiver 3 connected to the ultrasound probe 1, an image producer 4 is connected to the transmitter/receiver 3, and a display unit 6 is connected to the image producer 4 through the display controller 5. A candidate vascular wall boundary point determiner 7, a boundary determiner 8, and an IMT calculator 9 are sequentially connected to the transmitter/receiver 3, and the IMT calculator 9 is connected to the display controller 5. Further, the transmitter/receiver 3, the image producer 4, the candidate vascular wall boundary point determiner 7, the boundary determiner 8, and the IMT calculator 9 are connected to a controller 10. The controller 10 is connected to an operation input unit 11. The candidate vascular wall boundary point determiner 7 is provided with a temporary boundary position designation unit 12 therein, and the boundary determiner 8 is provided with a first evaluation value calculator 14, a second evaluation value calculator 15, and a third evaluation value calculator 16 therein.

The transmitter/receiver 3 is embedded with a transmission circuit and a reception circuit. The transmission circuit includes a plurality of channels and produces a plurality of actuation signals which are respectively applied to a plurality of ultrasound transducers of the ultrasound probe 1. At this time, the delay amount of each of the actuation signals is adjusted based on a transmission delay pattern selected according to a control signal from the controller 10 so that the ultrasonic waves transmitted from a plurality of ultrasound transducers form an ultrasonic beam, and a plurality of actuation signals with the adjusted delay amount are supplied to the ultrasound probe 1.

The reception circuit of the transmitter/receiver 3 includes a plurality of channels, receives and amplifies a plurality of analog reception signals which are respectively output from a plurality of ultrasound transducers, and converts the analog reception signals to digital reception signals. Further, the reception circuit performs reception focus processing (also referred to as phase matching) by giving respective delay times according to focus positions to a plurality of reception signals based on a reception delay pattern selected according to a control signal from the controller 10 and adding these reception signals for each focus position. With this reception focus processing, the focus of the ultrasonic echo is narrowed to produce a plurality of sound ray signals.

Next, envelope detection processing (also referred to quadrature detection processing) is performed on the sound ray signals by low pass filter processing or the like, and correction of attenuation due to the distance according to the depth of the reflection position of the ultrasonic wave is performed by STC (Sensitivity Time Gain Control).

The sound ray signals processed in the above-described manner are output to the image producer 4 and the candidate vascular wall boundary point determiner 7, and are sequentially stored in a data memory which has memory capacity enough to store sound ray signals for a plurality of frames. Here, the sound ray signal refers to a signal which has a value obtained by calculating, for example, $\{I^2(i,j)+Q^2(i,j)\}^{1/2}$ for each line (where i=1 to L: L is the total number of lines) and each depth direction sample point j (where j=1 to N: N is the total number of sampling points) in an IQ signal obtained by performing phase matching and quadrature detection processing on the reception signal and follows the j direction while i is fixed. It is to be noted that, instead of the above-described sound ray signal $(I^2(i,j)+Q^2(i,j))^{1/2}$, $I^2(i,j)+Q^2(i,j)$ or the like may be used. The intensity of the sound ray signal is not limited to the value of $\{I^2(i,j)+Q^2(i,j)\}^{1/2}$, and includes mathematically transformed values with no change in relative order of intensity at a sampling position of a sound ray, such as a value of a power of the above-described sound ray signal, a value obtained by multiplying the above-described sound ray signal by a predetermined coefficient, and a logarithmic value (logarithmic intensity).

The image producer 4 includes an image data producing function, receives sound ray signals directly supplied from the reception circuit of the transmitter/receiver 3 in a live mode and sound ray signals supplied from the data memory in a freeze mode as input, performs preprocessing, such as Log (logarithmic) compression or gain adjustment, on these sound ray signals, and produces image data representing the ultrasound image of the blood vessel. Then, produced image data of the ultrasound image is raster-converted to image data according to a normal television signal scan system, and the image data is subjected to necessary image processing, such as gradation processing, and is supplied to the display controller 5.

The display controller 5 controls the display unit 6 to display the ultrasound image of the blood vessel based on the image data supplied from the image producer 4. The display unit 6 includes, for example, a display device, such as an LCD, and displays the ultrasound image under the control of the display controller 5.

Meanwhile, the candidate vascular wall boundary point determiner 7 connected to the transmitter/receiver 3 determines the candidate vascular wall boundary points of the intima-media complex (vascular wall) of the blood vessel extending in a scan direction in the ultrasound image on the sound ray based on the sound ray signal supplied from the reception circuit of the transmitter/receiver 3, and outputs the result to the boundary determiner 8.

In addition, the candidate vascular wall boundary point determiner 7 includes a temporary boundary position designation unit 12 configured to designate the temporary vascular wall boundary positions (temporary lumen-intima boundary position and temporary media-adventitia boundary position) of the intima-media complex on the above-described sound ray in the ultrasound image displayed on the display unit 6 in response to an instruction of an operator from the operation input unit 11 through the controller 10. A search depth range for the candidate vascular wall boundary points on the sound ray is set based on the temporary lumen-intima boundary position and the temporary media-adventitia boundary position designated by the temporary boundary position designation unit 12.

<Determination of Candidate Vascular Wall Boundary Points>

The candidate vascular wall boundary point determiner 7 determines the candidate vascular wall boundary points within the determined search depth range for the candidate vascular wall boundary points. For example, as a candidate lumen-intima boundary point which is a candidate vascular wall boundary point, one or more candidate points are lined up for one sound ray.

The candidate vascular wall boundary point determiner 7 may determine the candidate vascular wall boundary points based on, for example, the intensity distribution of the above-described sound ray signal.

The boundary determiner 8 determines one lumen-intima boundary point (vascular wall boundary point) from one or more candidate lumen-intima boundary points lined up for one sound ray in the candidate vascular wall boundary point determiner 7, and determines a lumen-intima boundary (vascular wall boundary) based on the lumen-intima boundary point. The determination of the vascular wall boundary by the boundary determiner 8 is performed based on a third evaluation value calculated by the third evaluation value calculator 16 from a first evaluation value in the first evaluation value calculator 14 and a second evaluation value in the second evaluation value calculator 15.

It candidate vascular wall boundary positions (depth) $b_i(j)$ corresponding to the boundary of an intima-media complex of a sound ray $L_i$ are finite discrete positions (for example, $\{a_1, a_2, \ldots, a_{j-1}, a_j, \ldots a_n\}$), vascular wall (intima-media complex) boundary candidates (polygonal lines having L nodes) of L lines (L sound rays) are expressed by Expression (1).

$$B(b_i(j)) = (b_1(j), b_2(j), \ldots, b_{i-1}(j), b_i(j), \ldots, b_L(j)) \quad (1)$$

However, it is assumed that j in Expression (1) means the positions of one or more candidate vascular wall boundary points in each line from the first line to the L-th line.

<Calculation of First Evaluation Value>

The first evaluation value calculator 14 calculates a first evaluation value representing accuracy of each of the candidate vascular wall boundary points as a vascular wall boundary point for each sound ray by means of a sound ray signal corresponding to each sound ray.

For example, a point of interest having a predetermined feature amount highly relevant to the candidate vascular wall boundary points is found, and the first evaluation value can be calculated from the positional relationship with the point of interest. The predetermined feature amount may be extracted using the intensity of the sound ray signal or the intensity itself may be set as a predetermined feature amount.

For example, there is a method of calculating the first evaluation value based on the distance from a position which is shallower in a predetermined ratio than a depth position giving the intensity maximum value of the sound ray signal and which is in the vicinity of the intensity maximum value.

Figure 2:
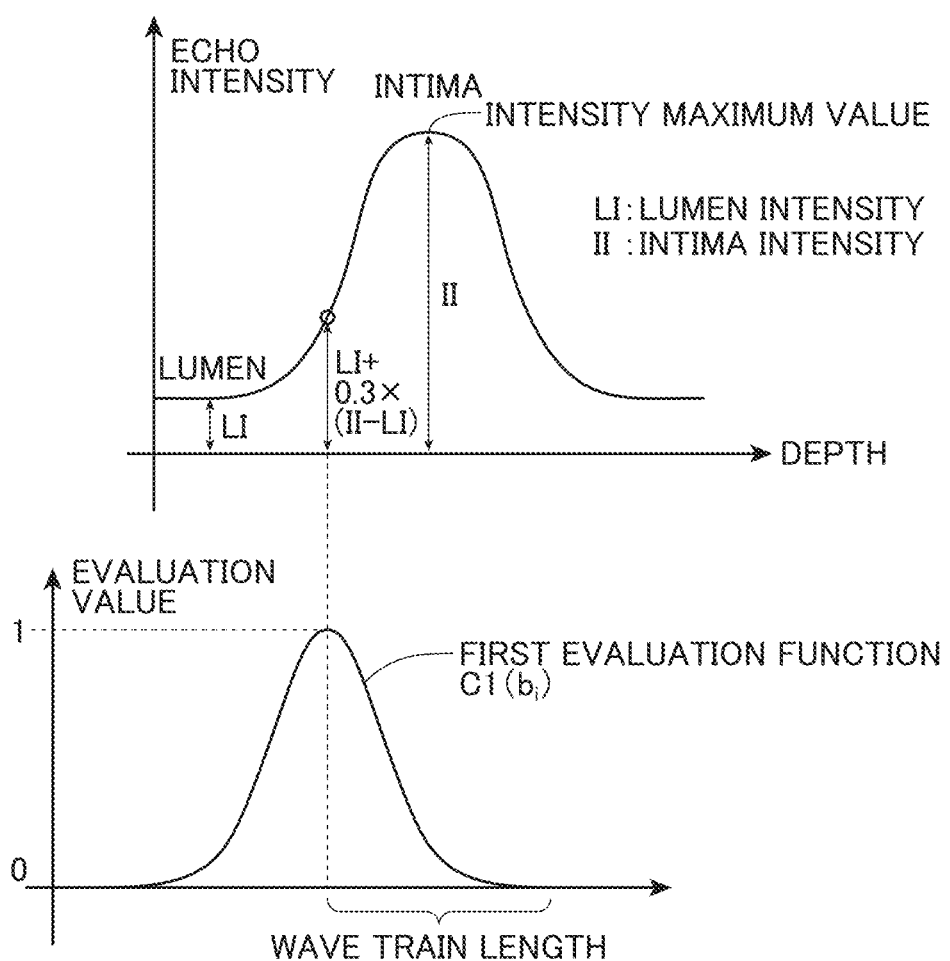
FIG. 2 is a graph showing an example of a first evaluation function for calculating a first evaluation value.

Specifically, the first evaluation value which represents accuracy of each of the candidate vascular wall boundary points as the vascular wall boundary point is calculated based on a first evaluation function $C1(b_i(j'))$ which takes a maximum value at a 30% intensity position of the intensity maximum value (for example, the maximum value of the logarithmic intensity) of the sound ray signal within the search depth range, attenuates as a distance from the 30% intensity position becomes far and becomes zero at a position separated from the 30% intensity position by about a wave train length of the transmission wave at the time of the transmission and reception of the ultrasonic beam, as shown in FIG. 2. Taking the maximum value at the 30% intensity position of the intensity maximum value is an example, and the first evaluation function which preferably takes the maximum value at a 10% intensity position to an 80% intensity position, and more preferably, at a 20% intensity position to a 70% intensity position may be appropriately determined.

<Calculation of Second Evaluation Value>

The second evaluation value calculator 15 calculates a second evaluation value which represents similarity (the deviation of the intensity distribution of the sound ray signals) between a sound ray signal corresponding to a sound ray of interest and a sound ray signal corresponding to any one of sound rays adjacent to the sound ray of interest.

For example, the second evaluation value is calculated based on the second evaluation function $C2(b_{i-1}(j), b_i(j'))$ of Expression (2) which is expressed using a normalized cross-correlation coefficient.

[Equation 3]

$$C2(b_{i-1}(j), b_i(j')) = \frac{\sum_{k=0}^{WL-1}\left\{f[i-1, j+k] - \left(\sum_{k=0}^{WL-1} f[i-1, j+k]/WL\right)\right\}\left\{f[i, j'+k] - \left(\sum_{k=0}^{WL-1} f[i, j'+k]/WL\right)\right\}}{\sqrt{\sum_{k=0}^{WL-1}\left\{f[i-1, j+k] - \left(\sum_{k=0}^{WL-1} f[i-1, j+k]/WL\right)\right\}^2} \sqrt{\sum_{k=0}^{WL-1}\left\{f[i, j'+k] - \left(\sum_{k=0}^{WL-1} f[i, j'+k]/WL\right)\right\}^2}}$$

(2)

In Expression (2), it is assumed that a candidate vascular wall boundary point $b_{i-1}(j)$ is in a sampling point (depth position) j on an (i−1)th sound ray, and a candidate vascular wall boundary point $b_i(j')$ is in a sampling point j' on an i-th sound ray. In addition, k represents a vascular wall boundary search depth range, and is about the wave train length WL of the transmission wave. Further, f[i,j] is the intensity (intensity after detection) of a sound ray signal on a sampling point (i,j). The deviation of the intensity distribution of the sound ray signals corresponding to sound rays is calculated by Expression (2) which subtracts the average value of the intensity of the sound ray signals from the value of the intensity of each sound ray signal, thereby stably calculating the correlation between adjacent sound rays, namely the similarity between adjacent sound rays even if intensity fluctuates.

<Calculation of Third Evaluation Value>

The third evaluation value calculator 16 calculates a function $C(b_i(j'))$ by Expression (3) from the above-described first evaluation function $C1(b_{i-m}(j))$ of the sound ray signal and the above-described second evaluation function $C2(b_{i-1}(j),b_i(j'))$ of the sound ray signal for the candidate vascular wall boundary point $b_{i-m}(j)$ within the vascular wall boundary search depth range, and calculates a third evaluation value based on a third evaluation function $C_{sum}$ which represents the sum of the function $C(b_i(j'))$ for a plurality of boundary candidates consisting of combinations of candidate vascular wall boundary points in the scan direction by Expression (4).

$C(b_i(j'))=W1\cdot C1(b_{i-1}(j'))+W2\cdot C2(b_{i-1}(j),b_i(j'));W1,W2$: weighting function    (3)

[Equation 4]

$$C_{sum} = \sum_{i=1}^{N} C(b_i(j'))$$

(4)

When W1 and W2 are positive numbers, a combination of candidate vascular wall boundary points, in which the third evaluation value by the third evaluation function $C_{sum}$ becomes maximum, is selected as a vascular wall boundary point, and a vascular wall is determined. When W1 and W2 are negative numbers, a combination of candidate vascular wall boundary points, in which the third evaluation value by the third evaluation function $C_{sum}$ becomes minimum, is selected as a vascular wall boundary point, and a vascular wall is determined.

In the above-described definitions of $C1(b_i(j))$ and $C2(b_{i-1}(j),b_i(j'))$ which are used as an evaluation function in calculating the vascular wall boundary, when the respective values of $C1(b_i(j))$ and $C2(b_{i-1}(j),b_i(j'))$ become larger, accuracy as a candidate vascular wall boundary point becomes higher. However, for example, in the case where $C1(b_i(j))$ and $C2(b_{i-1}(j),b_i(j'))$ are respectively defined as the reciprocal of the above-described definitions, when the respective values become smaller, accuracy as a candidate vascular wall boundary point becomes higher.

Accordingly, in the case where the functions are defined so that when the first evaluation value and the second evaluation value become smaller, accuracy as a candidate vascular wall boundary point becomes larger, if W1 and W2 are positive numbers, in a selected combination of candidate vascular wall boundary points (vascular wall boundary), a vascular wall boundary point is selected from a combination of candidate vascular wall boundary points in which the third evaluation value by the third evaluation function $C_{sum}$ becomes minimum, and a vascular wall is determined. If W1 and W2 are negative numbers, in a selected combination of candidate vascular wall boundary points (vascular wall boundary), a vascular wall boundary point is selected from a combination of candidate vascular wall boundary points in which the third evaluation value by the third evaluation function $C_{sum}$ becomes maximum, and a vascular wall is determined.

In Expressions (2) to (4), although the correlation between adjacent sound rays is calculated, the invention is not limited thereto, and the correlation between separate sound rays, for example, two sound rays with one to four sound rays therebetween may be calculated. That is, $C2(b_{i-m}(j),b_i(j'))$ (where i>i−m>0, m is a natural number) may be calculated.

In the selection of the vascular wall boundary, for example, when the candidate vascular wall boundary position (depth) $b_i(j')$ takes a finite number of discrete positions (such as n discrete positions) for one sound ray, normally, it is necessary to calculate $C_{sum}$ for L lines, that is, $n^L$ in combination. However, by using the dynamic programming method, the amount of calculation can be significantly reduced. This will be described below in detail.

Information of the depth position of the determined boundary of the intima-media complex is output to the IMT calculator 9.

The IMT calculator 9 calculates the intima-media thickness (IMT) based on the depth position of the boundary of the intima-media complex determined by the boundary determiner 8. The calculated intima-media thickness is displayed on the display unit 6 through the display controller 5.

Although the display controller 5, the controller 10, the respective determiners, and the like are constituted by a CPU, an operation program stored in a memory to cause the CPU to perform various kinds of processing, a memory for data storage, various buses through which data is exchanged, and the like, these may be constituted by digital circuits.

<Operation>

Next, the operation of Embodiment 1 will be described.

Figure 3:
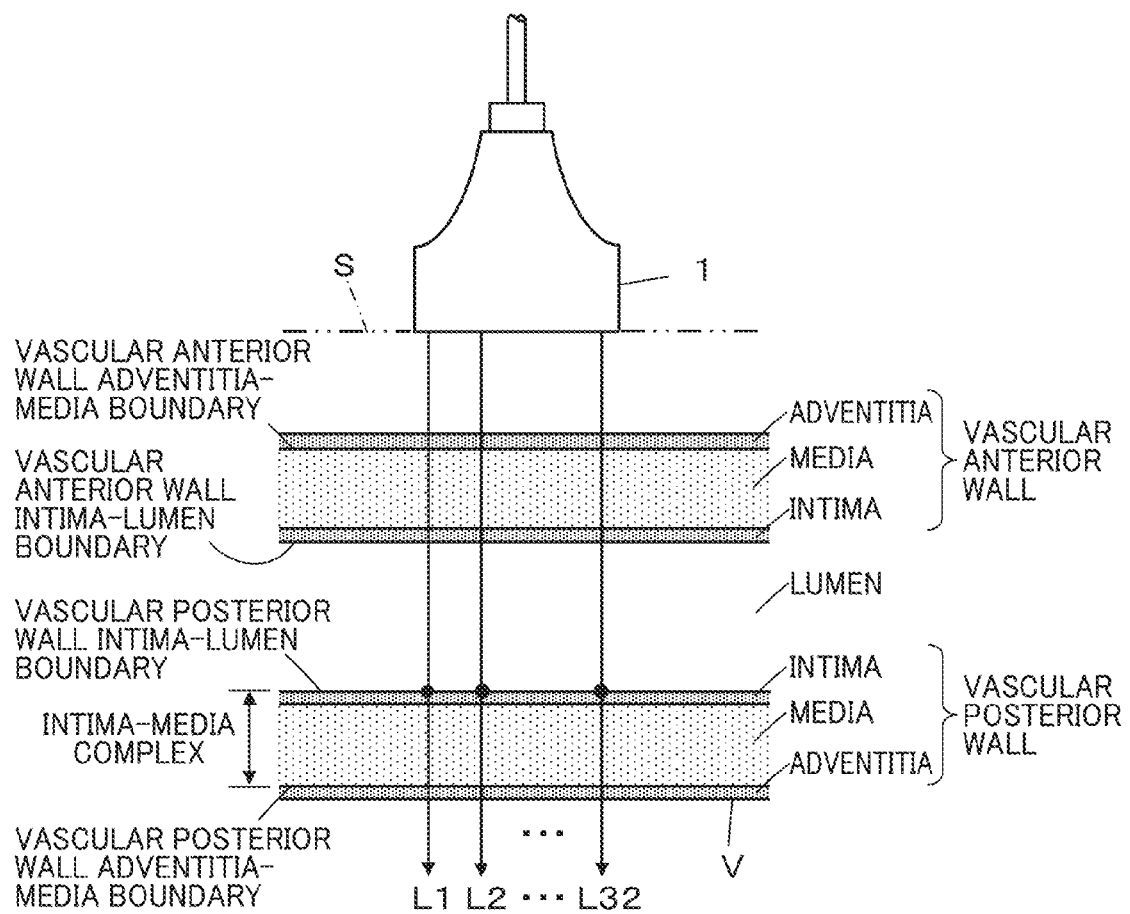
FIG. 3 is a diagram showing a mode of a sound ray produced by transmission and reception of an ultrasonic beam with respect to a blood vessel.

First, as shown in FIG. 3, if the ultrasound probe 1 is placed to be in contact with the body surface of a subject S, an ultrasonic beam is transmitted from the ultrasound probe 1 toward a blood vessel in the subject S in response to an actuation signal from the transmission circuit of the transmitter/receiver 3 in the diagnostic apparatus body 2. The ultrasonic beam which is incident on the blood vessel V is reflected by the respective portions of the vascular wall, and an ultrasonic echo is received by each of the ultrasound transducers of the ultrasound probe 1.

If the ultrasonic echo is received by each of the ultrasound transducers, a reception signal according to the intensity of the ultrasonic echo is output from each of the ultrasound transducer to the reception circuit of the transmitter/receiver 3. The reception circuit produces sound ray signals corresponding to a plurality of sound rays arranged in the scan direction, for example, 32 sound rays L1 to L32 based on the reception signals output from the ultrasound transducers. The produced sound ray signals of the sound rays L1 to L32 are output from the transmitter/receiver 3 to the image producer 4.

The image producer 4 produces image data of the blood vessel V based on the intensity distribution of the input sound ray signals of the sound rays L1 to L32. The produced image data is then subjected to necessary image processing such as gradation processing, and is then output to the display controller 5, and for example, an ultrasound image (B-mode tomographic image) shown in FIG. 4 is displayed on the display unit 6.

Meanwhile, the reception circuit of the transmitter/receiver 3 outputs the produced sound ray signals corresponding to the sound rays L1 to L32 to the candidate vascular wall boundary point determiner 7. The candidate vascular wall boundary point determiner 7 determines the candidate vascular wall boundary points for each sound ray based on the intensity distribution of the sound ray signals of the sound rays L1 to L32 supplied from the transmitter/receiver 3. Here, the boundary of the intima-media complex is constituted by the boundary between the intima of the vascular posterior wall and the lumen (vascular posterior wall intima-lumen boundary), the boundary between the adventitia and the media of the vascular posterior wall (vascular posterior wall adventitia-media boundary), the boundary between the adventitia and the media of the vascular anterior wall (vascular anterior wall adventitia-media boundary), and the boundary between the intima of the vascular anterior wall and the lumen (vascular anterior wall intima-lumen boundary).

Figure 4:
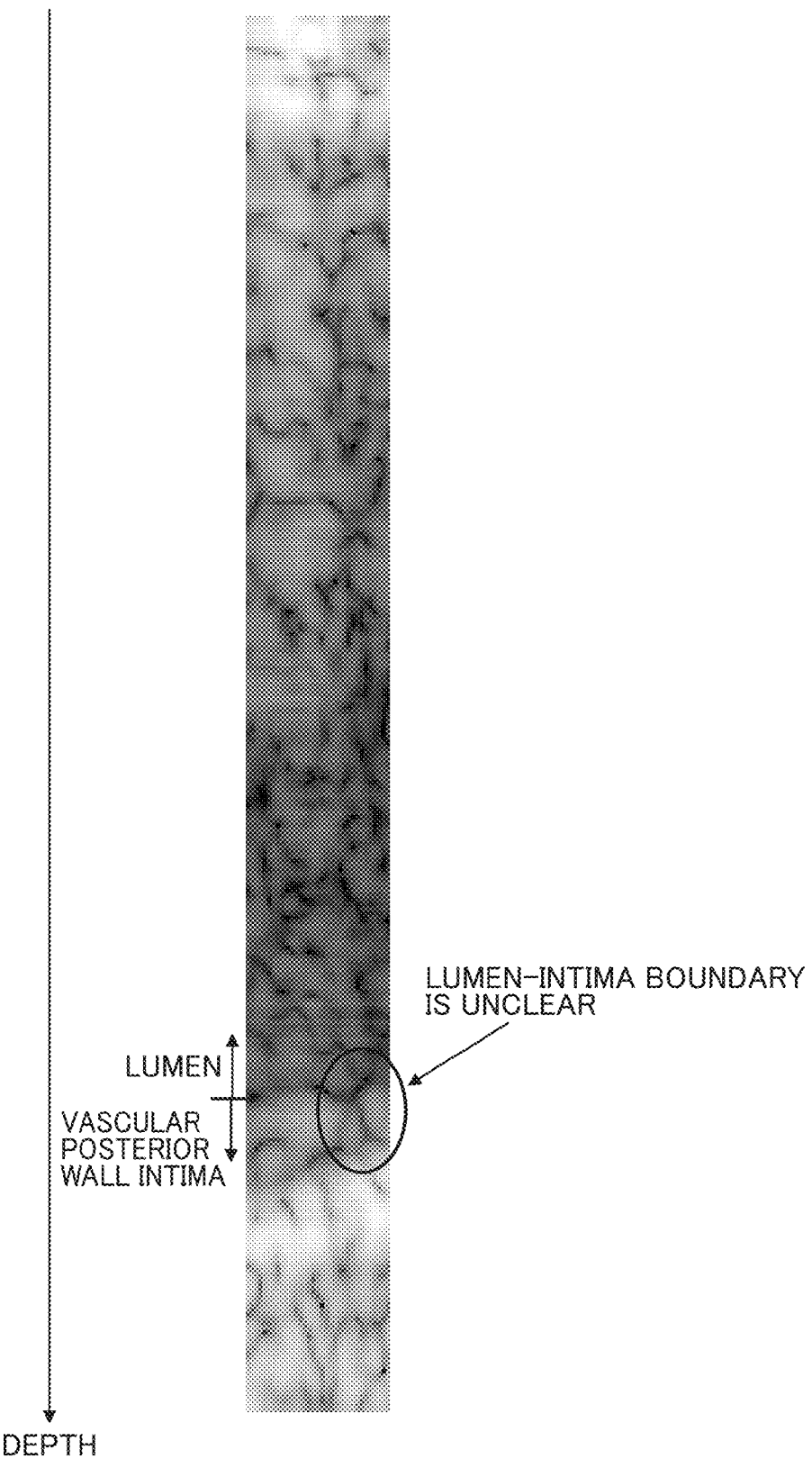
FIG. 4 is a diagram showing an ultrasound image of a blood vessel including a lumen-intima boundary, which is a vascular wall.

FIG. 4 shows a B-mode tomographic image displayed on the display unit 6 as described above. As shown in FIG. 4, while a vascular posterior wall intima-lumen boundary can be confirmed on the left side of the image, the boundary seems to be branched into two directions on the right side of the image, and thus, the lumen-intima boundary is unclear.

Figure 5:
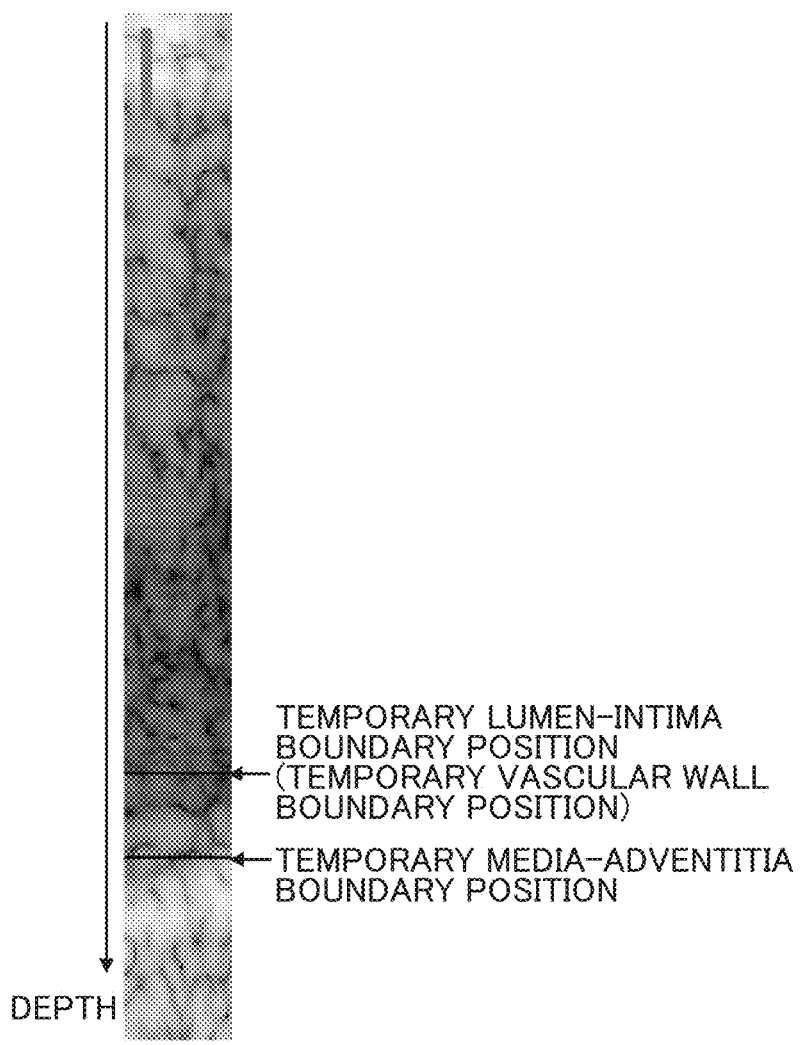
FIG. 5 is an explanatory view of a case of designating a temporary vascular wall boundary position (temporary lumen-intima boundary position and temporary media-adventitia boundary position) in the ultrasound image of the blood vessel shown in FIG. 4.

Next, as shown in FIG. 5, the operator operates the operation input unit 11 to designate a temporary lumen-intima boundary position (temporary vascular wall boundary position) through the temporary boundary position designation unit 12 of the candidate vascular wall boundary point determiner 7 in the B-mode tomographic image displayed on the display unit 6. This allows a temporary lumen-intima boundary position to be designated for sound rays corresponding to the B-mode tomographic image. A temporary media-adventitia boundary position is designated at a position separated for a predetermined depth by the temporary boundary position designation unit 12 of the candidate vascular wall boundary point determiner 7 based on the temporary lumen-intima boundary position of the B-mode tomographic image displayed on the display unit 6. The temporary media-adventitia boundary position may be automatically determined based on the temporary lumen-intima boundary position, or similarly to the temporary lumen-intima boundary position, the operator may operate the operation input unit 11 to designate the temporary media-adventitia boundary position through the temporary boundary position designation unit 12 of the candidate vascular wall boundary point determiner 7.

Figure 6:
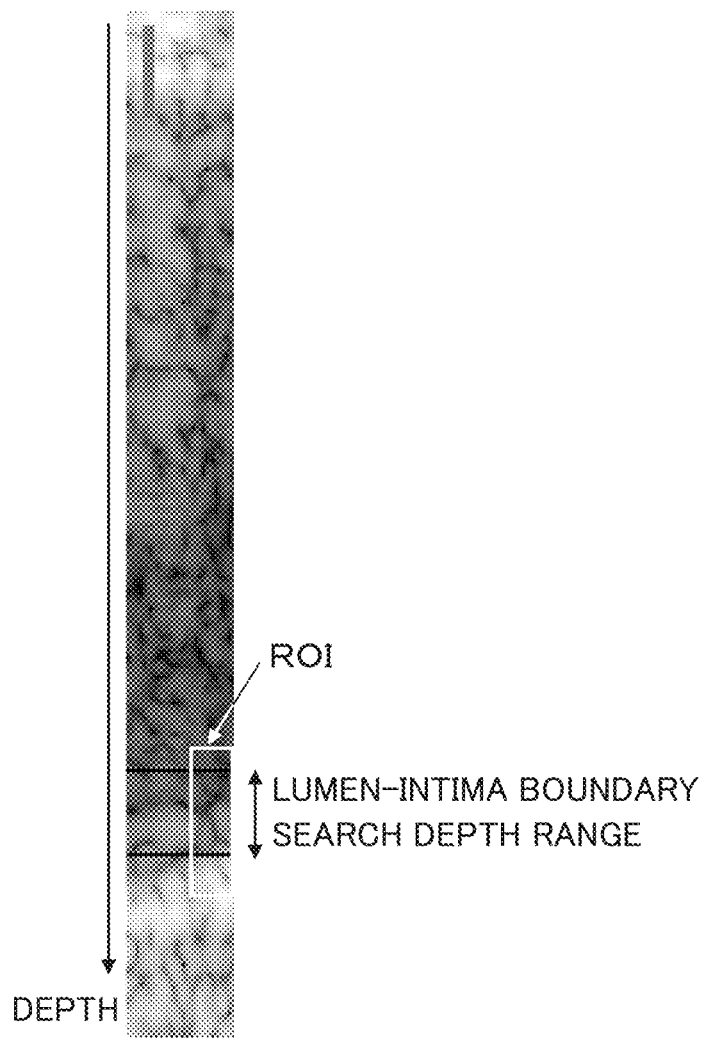
FIG. 6 is an explanatory view of a case where a region of interest (ROT) and a vascular wall search depth range are set in the ultrasound image of the blood vessel shown in FIG. 4.

As shown in FIG. 6, a lumen-intima boundary search depth range is set based on the temporary lumen-intima boundary position and the temporary media-adventitia boundary position designated by the temporary boundary position designation unit 12 of the candidate vascular wall boundary point determiner 7. For description, a partial region including the lumen-intima boundary search depth range is referred to as a region of interest ROI.

Figure 7:
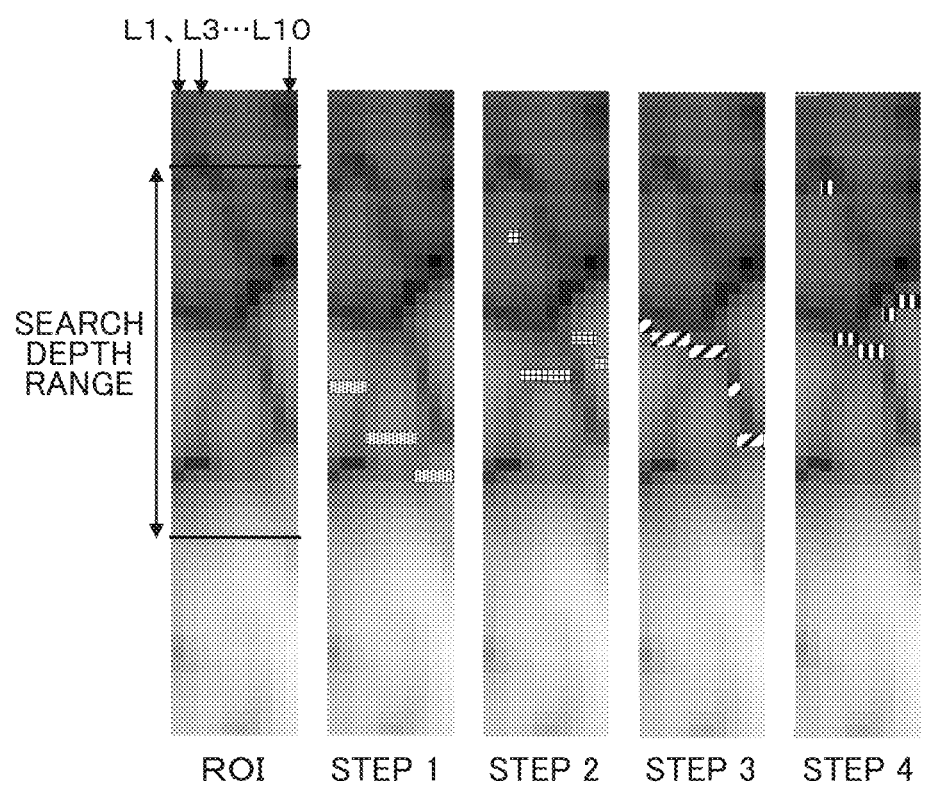
FIGS. 7A to 7E are explanatory views illustrating steps of searching for boundary position candidates in the vascular wall search depth range.

FIG. 7A is an enlarged view of the region of interest ROI extracted from the B-mode tomographic image shown in FIG. 6. The region of interest ROI shown in FIG. 7A is constituted by sound rays L1 to L10.

FIGS. 7B to 7E are explanatory views illustrating respective steps of determining candidate vascular wall boundary points in the candidate vascular wall boundary point determiner 7.

In Step 1, for example, a maximum point giving the maximum value of the logarithmic intensity is detected by the candidate vascular wall boundary point determiner 7 on each of the sound rays L1 to L10 within the vascular wall search depth range. A place highlighted in a rectangular portion in FIG. 7B is the maximum point giving the maximum value of the logarithmic intensity.

Next, in Step 2, a point which exists at a place shallower than the maximum point giving the maximum value of the logarithmic intensity detected in Step 1 and separated from the maximum point more than half the wave train length of the transmission wave at the time of the transmission and reception of the ultrasonic beam and which has a local maximum value equal to or greater than 75% of the maximum value of the logarithmic intensity (equal to or greater than a first threshold value) is detected within the vascular wall search depth range as a shallow portion local maximum point. A place highlighted in a rectangular portion in FIG. 7C is the shallow portion local maximum point. Depending on the sound ray, there is a case where no shallow portion local maximum point exists.

Next, in Step 3, a point which exists at a place shallower than the maximum point giving the maximum value of the logarithmic intensity detected in Step 1 and within a length of half the wave train length of the transmission wave at the time of the transmission and reception of the ultrasonic beam from the maximum point and which has logarithmic intensity of about 80% of the maximum value (second threshold value) is detected within the vascular wall search depth range as a first point of interest. A place highlighted in a rectangular portion in FIG. 7D is the first point of interest.

Finally, in Step 4, a point which exists at a place shallower than the shallow portion local maximum point detected in Step 2 and within a length of half the wave train length of the transmission wave at the time of the transmission and reception of the ultrasonic beam from the shallow portion local maximum point and which has logarithmic intensity of about 80% of the local maximum value as the value of the shallow portion local maximum point (third threshold value) is detected within the vascular wall search depth range as a second point of interest. A place highlighted in a rectangular portion in FIG. 7E is the second point of interest.

The candidate vascular wall boundary point determiner 7 outputs information regarding the first point of interest and the second point of interest calculated in the above-described manner to the boundary determiner 8 as candidate vascular wall boundary points.

Figure 8:
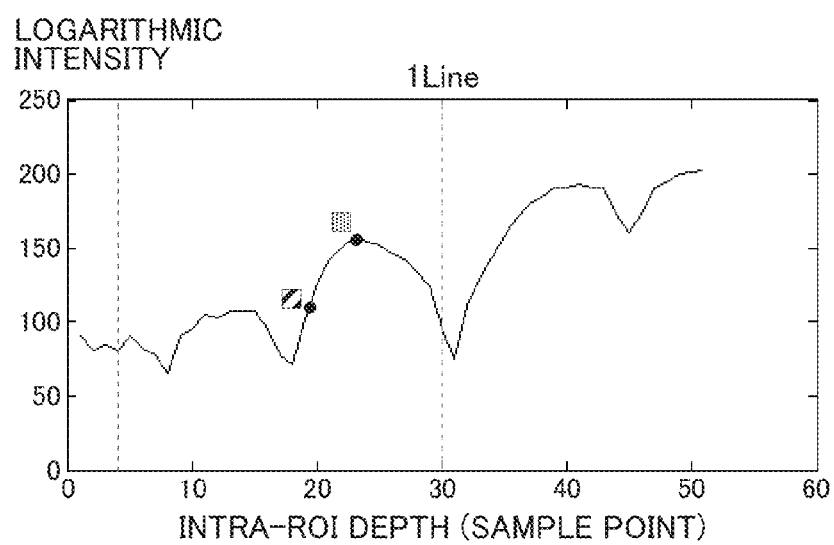
FIG. 8 is a graph showing a profile of a first line (L1) (first sound ray) in the vascular wall search depth range shown in FIGS. 7A to 7E.
Figure 9:
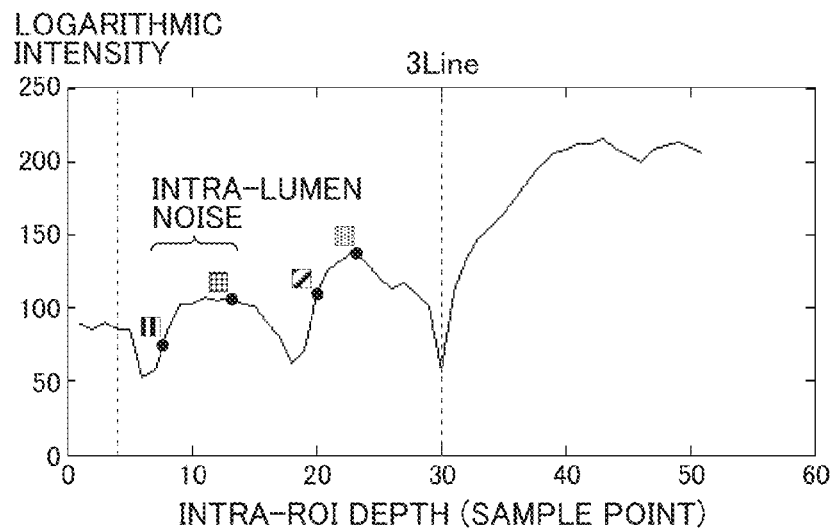
FIG. 9 is a graph showing a profile of a third line (L3) (third sound ray) in the vascular wall search depth range shown in FIGS. 7A to 7E.
Figure 10:
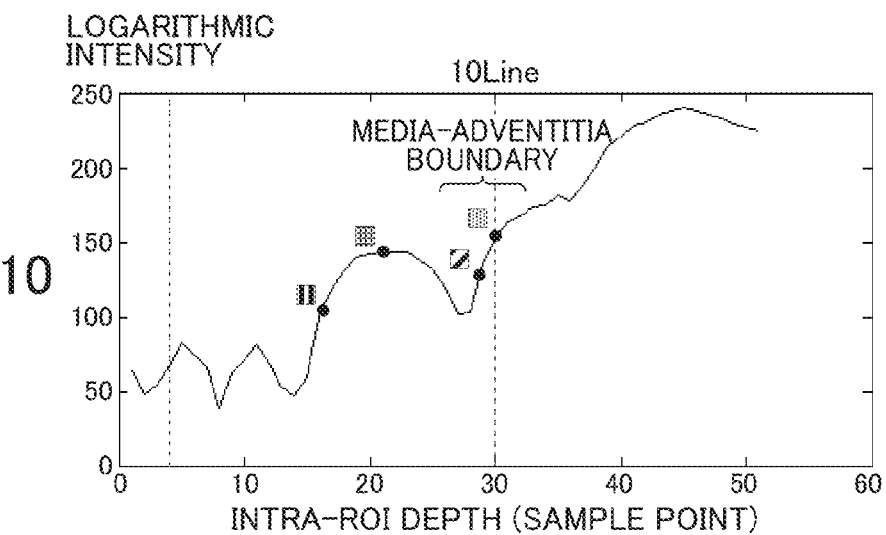
FIG. 10 is a graph showing a profile of a tenth line (L10) (tenth sound ray) in the vascular wall search depth range shown in FIGS. 7A to 7E.

The profiles of the sound rays L1, L3, and L10 are shown in the graphs of FIGS. 8 to 10.

As shown in FIG. 8, in the sound ray L1, only a maximum point and a first point of interest are detected, and a shallow portion local maximum point and a second point of interest are not detected. As shown in FIG. 9, in the sound ray L3, noise in a lumen (erroneous detection) and a lumen-intima boundary are detected as candidate vascular wall boundary points, and in the sound ray L10 shown in FIG. 10, a lumen-intima boundary and a media-adventitia boundary (erroneous detection) are detected as candidate vascular wall boundary points.

FIGS. 11A and 11B are detailed explanatory views of candidate vascular wall boundary points determined by the candidate vascular wall boundary position determiner. In particular, the candidate vascular wall boundary points in the sound rays L8 to L10 are divided into two kinds.

FIG. 12 is an explanatory view showing combinations of candidate vascular wall boundary points calculated in the boundary determiner 8. The boundary determiner 8 calculates the first evaluation value in the first evaluation value calculator 14 and the second evaluation value in the second evaluation value calculator 15 for each of the candidate vascular wall boundary points, and calculates the third evaluation value in the third evaluation value calculator 16 based on the first evaluation value and the second evaluation value.

In order to select a combination of candidate vascular wall boundary points in which the third evaluation value becomes maximum, the first evaluation value and the second evaluation value in each candidate point may be calculated, and the third evaluation value for all combinations of candidate vascular wall boundary points may be calculated based on the first evaluation value and the second evaluation value, or the evaluation values may be calculated using the dynamic programming method as described above.

<Dynamic Programming Method>

Next, a method of calculating the third evaluation function using the dynamic programming method will be described in detail.

For simplification of the description of the dynamic programming method, a case where the number of lines is ten, the number of sampling points of each line is ten, and all sampling points are selected as candidate vascular wall boundary points will be described. It is assumed that, as the second evaluation value, similarity (correlation) between adjacent sound rays is calculated.

First, the first evaluation value is calculated as $C1(b_i(j))$ by the above-described method. The second evaluation value is calculated as $C2(b_{i-1}(j),b_i(j'))$ by the above-described method.

$C1(b_i(j'))$ and $C2(b_{i-1}(j),b_i(j'))$ define evaluation functions and are evaluation values which can be calculated as values associated with the respective sampling points. On the above-described assumption, $C1(b_i(j'))$ is provided for each sample point, and $C2(b_{i-1}(j),b_i(j'))$ is provided for each sampling point excluding the first line, that is, ten evaluation values are provided as evaluation values corresponding to one of ten sample points of an adjacent line. That is, if a certain line is considered, 10×10 evaluation values of $C2(b_{i-1}(j),b_i(j'))$ are calculated.

In the dynamic programming method, $b_i(j')$ in which $C_{sum}$ becomes maximum is determined as follows, thereby determining a vascular wall boundary point among candidate vascular wall boundary points.

$$C_{sum} = C1(b_i(j)) + \{C1(b_2(j)) + C2(b_i(j), b_2(j'))\} + \{C1(b_3(j)) + C2(b_2(j), b_3(j'))\} + \ldots + \{C1(b_{10}(j)) + C2(b_9(j), b_{10}(j'))\} \quad (5)$$

How to determine a combination of $b_i(j')$ in which $C_{sum}$ is maximized will be described specifically.

For simplification of the expression, if $H(b_{i-1}(j),b_i(j'))=C1(b_i(j))+C2(b_{i-1}(j),b_i(j'))$. (A), Expression (5) becomes as follows.

$$C_{sum} = C1(b_i(j)) + H(b_1(j), b_2(j')) + H(b_2(j), b_3(j')) + \ldots + H(b_9(j), b_{10}(j')) \quad (6)$$

First, attention is focused on $b_i(j)$. This concerns only $C1(b_i(j))$ and $H(b_1(j),b_2(j'))$. Accordingly, $b_1(j)$ may be selected so that $C1(b_i(j))+H(b_1(j),b_2(j'))$ becomes maximum. Therefore, optimum $b_1(j)$ is calculated for all possible values of $b_2(j')$. This is regarded as a function of $b_2(j')$ and can be written as $b_1(j,b_2(j'))$. Since the maximum value of $C1(b_i(j))+H(b_1(j),b_2(j'))$ depends on $b_2(j')$, $C1(b_i(j))+H(b_1(j),b_2(j'))$ is regarded as a function of $b_2(j')$ and defined as follows.

$$D2(b_2(j')) = \max[C1(b_1(j)) + H(b_1(j), b_2(j')), b_1(j)]$$
$$= \max[C1(b_1(j, b_2(j'))) + H(b_1(j, b_2(j')), b_2(j')), b_1(j, b_2(j'))]$$

If this is used, Expression (6) can be written as follows.

$$C_{sum} = D2(b_2(j')) + H(b_2(j), b_3(j')) + \ldots + H(b_9(j), b_{10}(j')) \quad (7)$$

With this, it is possible to reduce one variable in the same form as Expression (6). Accordingly, the same procedure is sequentially repeated, thereby reducing variables one by one. That is, if the function $D3(b_3(j'))$ is defined as follows, $D3(b_3(j'))=\max[D2(b_2(j))+H(b_2(j),b_3(j')),b_2(j)]$ and $b_2(j)$ giving the maximum value is written as $b_2(j,b_3(j'))$, the expression can be written as the following expression.

$$D3(b_3(j')) = \max[D2(b_2(j,b_3(j'))) + H(b_2(j,b_3(j')),b_3(j')), b_2(j,b_3(j'))]$$

Accordingly, Expression (7) can be written as follows.

$$C_{sum} = D3(b_3(j)) + H(b_3(j), b_4(j')) + \ldots + H(b_9(j), b_{10}(j')) \quad (8)$$

Similarly, finally, if the function $D10(b_{10}(j'))$ is defined as follows, $$D10(b_{10}(j')) = \max[D9(b_9(j)) + H(b_9(j), b_{10}(j')), b_9(j)]$$

and $b_9(j)$ giving the maximum value is written as $b_9(j,b_{10}(j'))$, the expression can be written as the following expression.

$$D10(b_{10}(j'))=\max[D9(b_9(j,b_{10}(j')))+H(b_9(j,b_{10}(j')),b_{10}(j')),b_9(j,b_{10}(j'))]$$

Then, Expression (8) can be written as follows.

$$C_{sum}=D10(b_{10}(j')) \quad (9)$$

Accordingly, as shown in Expression (9), $C_{sum}$ becomes a one-variable function having one variable. The value of $b_{10}(j')$ in which the one-variable function $D10(b10(j'))$ becomes maximum is set as $b^*_{10}(j')$. The value $b^*_9(j)$ of optimum $b_9(j)$ is $b^*_9(j,b^*_{10}(j'))$. In a reverse order, the value $b^*_8(j)$ of $b_8(j)$ becomes $b^*_8(j,b^*_9(j'))$. Furthermore, in a reverse and sequential order, the value $b^*_1(j)$ of $b_1(j)$ can be determined as $b^*_1(j,b^*_2(j'))$.

A form in which the maximum value of $C_{sum}$ is calculated without using C1 after the second line is also possible. That is, the following expression may be defined, and the maximum value may be calculated in the same manner as the above description.

$$C_{sum}=C1(b_i(j))+C2(b_1(j),b_2(j'))+C2(b_2(j),b_3(j'))+\ldots+C2(b_{10}(j),b_{10}(j')) \quad (5')$$

This means that (Expression A) can be rewritten as $H(b_{i-1}(j),b_i(j'))=C2(b_{i-1}(j),b_i(j'))$, and the same calculation can be performed using the dynamic programming method.

Although in the above description, for simplification of the description of the dynamic programming method, a case where the number of lines is ten, the number of sampling points of each line is ten, and all sampling points are selected as candidate vascular wall boundary points has been described, it is of course general that the number of lines is L (a natural number equal to or greater than two) and the number of sampling points is N (a natural number equal to or greater than two).

Although a case where the number of sampling points of each line is ten, and all sampling points are selected as candidate vascular wall boundary points has been described, when the number of sampling points is N, instead of all sampling points, only candidate points which extracted as candidate vascular wall boundary points in advance may be selected among the N points, and calculation may be performed by the dynamic programming method. The number of candidate vascular wall boundary points may differ between the lines.

Although a case where the correlation between adjacent sound rays is calculated has been described, the invention is not limited thereto, and for example, the correlation between two lines with one to four lines therebetween may be calculated. That is, $C2(b_{i-m}(j),b_i(j'))$ (where i>i−m>0, m is a natural number) may be calculated.

The calculation may be performed by respectively multiplying $C1(b_i(j'))$ and $C2(b_{i-1}(j),b_i(j'))$ by W1 and W2 which are weighting coefficients.

Although a case where when the values of $C1(b_i(j'))$ and $C2(b_{i-1}(j),b_i(j'))$ become larger, accuracy as a candidate vascular wall boundary point becomes higher has been described, in the case where the evaluation functions which give higher accuracy as a candidate vascular wall boundary point when these evaluation functions become smaller is used, $D2(b_2(j'))$ to $D10(b_{10}(j'))$ may be changed to determine $b_{i-1}(j)$ and $b_i(j')$ in which the minimum value is obtained.

<Specific Example Based on Real Data>

An example in which a dynamic programming method using data actually obtained from the subject is used, and specifically, as shown in FIGS. 11A, 11B, and 12, a case where the number of candidate points of each line is two and the number of lines is three will be described.

$C1(b_8(8))=C1(b_8(14))=0.5$ is input as an initial value.

When $b_8(j)=\{8,14\}$, $b_9(j)=\{7,18\}$, and $b_{10}(j)=\{7,18\}$, it is assumed that the value of $C2(b_8(j),b_9(j'))$ is as in Table 1.

TABLE 1

|  | $b_9 = 7$ | $b_9 = 18$ |
|---|---|---|
| $b_8 = 8$ | 1.39 | 1.14 |
| $b_8 = 14$ | −0.008 | −0.19 |

TABLE 2

|  | $b_{10} = 7$ | $b_{10} = 18$ |
|---|---|---|
| $b_9 = 7$ | 0.86 | 0.12 |
| $b_9 = 18$ | 0.19 | 0.84 |

TABLE 3

|  | $b_{10} = 7$ | $b_{10} = 18$ |
|---|---|---|
| $b_9 = 7$ | 0.5 + 1.39 + 0.86 = 2.75 | 0.5 + 1.39 + 0.12 = 2.01 |
| $b_9 = 18$ | 0.5 + 1.14 + 0.19 = 1.83 | 0.5 + 1.14 + 0.84 = 2.47 |

However, $$D9(b_9(j'))=\max[D_8(b_8(j))+H(b_8(j),b_9(j')),b_8(j)]H(b_9(j),b_{10}(j'))=C2(b_9(j),b_{10}(j'))$$

At this time, from Table 3, it is understood that, when $b_{10}(j)=7$, the maximum value of 2.75 is taken. Accordingly, the vascular wall boundary point can be determined in a reverse order, that is, Table 3, Table 2, and Table 1. From Table 2, $b_9(j)=7$ is determined, and from Table 1, $b_8(j)=8$ is determined. That is, the vascular wall boundary point can be determined as $b_{10}(j)=7$, $b_9(j)=7$, and $b_8(j)=8$ among the candidate vascular wall boundary points.

<Application to IMT Measurement>

The third evaluation value is maximized when x1=8 in Line 8, x2=7 in Line 9, and x3=7 in Line 10, that is, $b=(b_8,b_9,b_{10})=(8,7,7)$ The lumen-intima boundary point and the media-adventitia boundary point are calculated based on the method of determining the vascular wall boundary point described above, and the lumen-intima boundary and the media-adventitia boundary are determined based on the lumen-intima boundary point and the media-adventitia boundary point. Information regarding the determined vascular wall is output to the IMT calculator 9.

The IMT calculator 9 calculates the intima-media thickness (IMT) of the vascular wall from the difference between the position of the determined lumen-intima boundary and the position of the media-adventitia boundary.

As described above, since it is possible to accurately determine the boundary of the intima-media complex in the ultrasound image, it is possible to measure the intima-media thickness based on the boundary with high precision.

Embodiment 2

Figure 13:
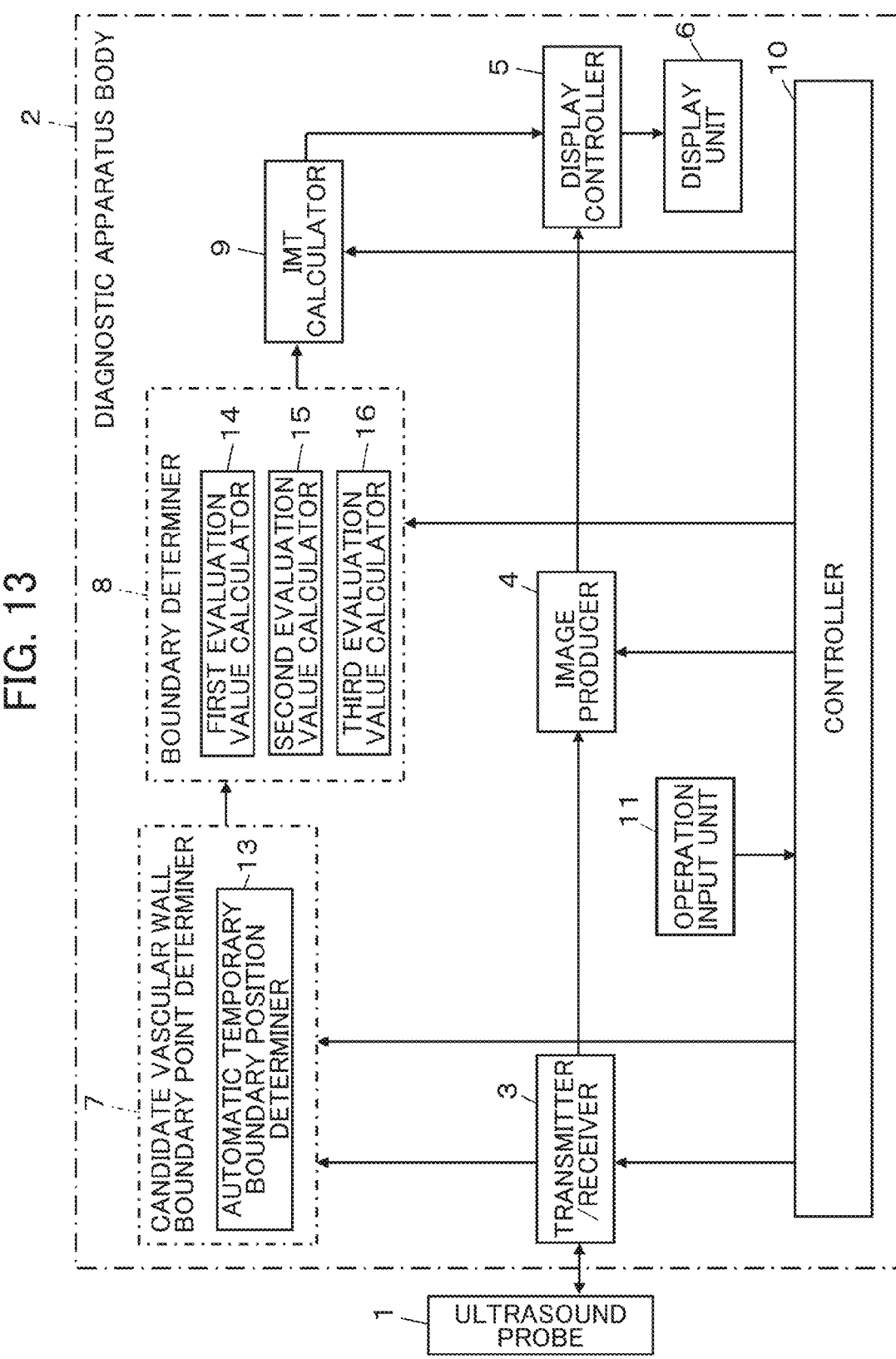
FIG. 13 is a block diagram showing the configuration of an ultrasound diagnostic apparatus according to Embodiment 2 of the invention.

FIG. 13 is a block diagram of an ultrasound diagnostic apparatus according to Embodiment 2 of the invention.

The ultrasound diagnostic apparatus according to Embodiment 2 is different from Embodiment 1 in that the candidate vascular wall boundary point determiner 7 of the diagnostic apparatus body 2 includes an automatic temporary boundary position determiner 13, instead of the temporary boundary position designation unit 12.

The candidate vascular wall boundary point determiner 7 includes the automatic temporary boundary position determiner 13 which automatically determines the temporary boundary positions (temporary lumen-intima boundary position and temporary media-adventitia boundary position) of the intima-media complex of the sound rays in response to an instruction of the operator from the operation input unit 11. As in Embodiment 1, a vascular wall boundary search depth range is set for the sound rays based on the determined temporary boundary positions.

The automatic determination of the temporary boundary positions by the automatic temporary boundary position determiner 13 may be performed using smoothed sound ray signals which are obtained by performing smoothing processing on sound ray signals in the scanning direction or depth direction.

Figure 14:
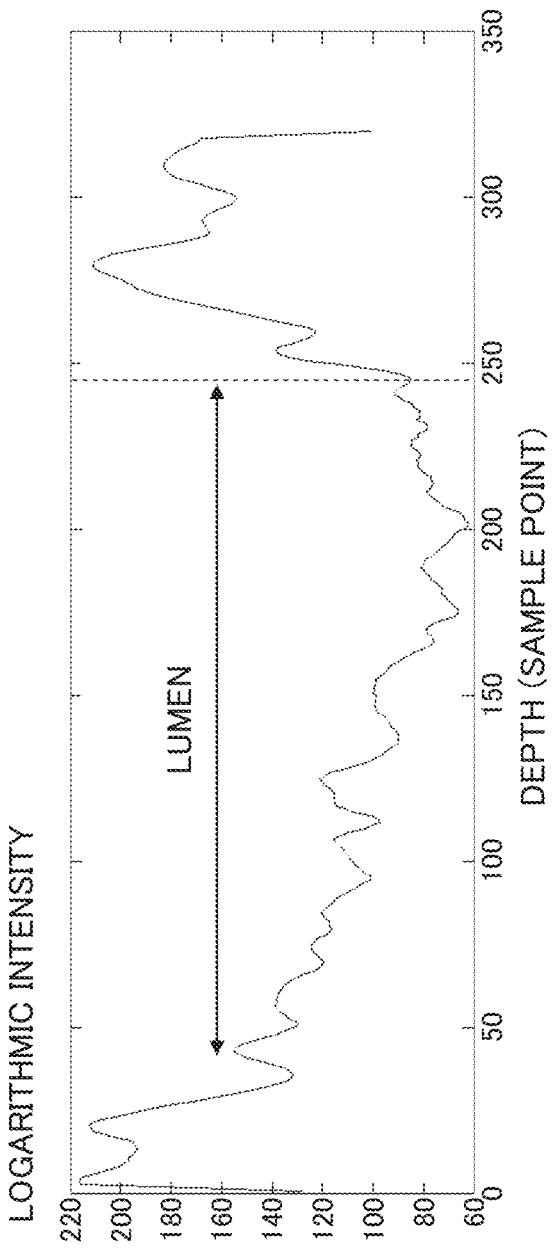
FIG. 14 is a graph showing a depth direction profile obtained in the ultrasound diagnostic apparatus according to Embodiment 2 of the invention, by averaging the luminance of the ultrasound image of the blood vessel shown in FIG. 4 in a scanning direction and expressing the result in logarithmic intensity.

FIG. 14 is a graph showing a profile in a depth direction obtained by taking an average of a plurality of sound rays in the scan direction and calculating the logarithmic intensity thereof. In the B-mode tomographic image showing the cross-section of the blood vessel, the lumen portion of the blood vessel can be clearly captured.

Figure 15:
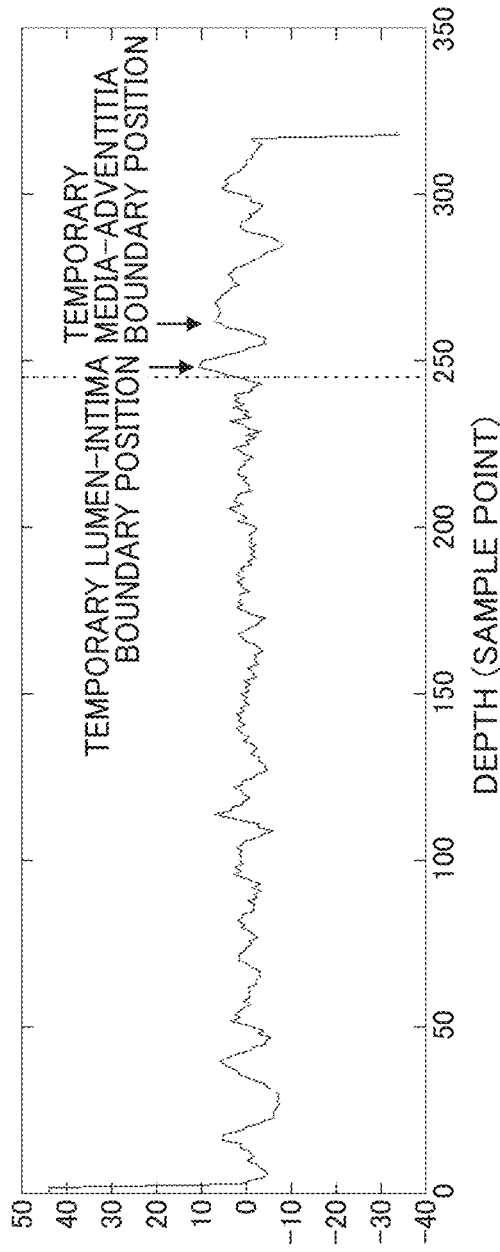
FIG. 15 is a graph showing a profile of an amount of change in logarithmic intensity per unit depth at a depth position in the depth direction profile shown in FIG. 14.

FIG. 15 is a graph showing a profile of an amount of change in logarithmic intensity per unit depth at a depth position with respect to the depth direction profile shown in FIG. 14.

In the automatic temporary boundary position determiner 13, a lumen is detected from the depth direction profile shown in FIG. 14, and based on the profile of the amount of change per unit depth shown in FIG. 15 and the position of the lumen, places deeper than the lumen for about several mm and at which the amount of change in luminance per unit depth is large are determined as a temporary lumen-intima boundary position and a temporary media-adventitia boundary position in order from the shallower side.

Subsequent operations are the same as in Embodiment 1.

As in Embodiment 1, since it is possible to accurately determine the boundary of the intima-media complex in the ultrasound image, it is possible to measure the intima-media thickness based on the boundary with high precision.

Modification Example

In Embodiment 1 and Embodiment 2, the first evaluation function $C1(b_i(j'))$ is calculated based on only the intensity maximum value of the sound ray signal. However, the first evaluation function $C1(b_i(j'))$ may be calculated based on a plurality of intensity values such as the intensity maximum value, the second largest intensity value, and the third largest intensity value, and predetermined number of first evaluation values selected in descendent order of intensity value and representing accuracy of each of the candidate vascular wall boundary points as the vascular wall boundary point may be calculated based on the first evaluation function $C1(b_i(j'))$ which, in each of the intensity values, takes a maximum value at a 30% intensity position of the intensity value, attenuates as a distance from the 30% intensity position becomes far and becomes zero at a position separated therefrom by about a wave train length of the transmission wave at the time of the transmission and reception of the ultrasonic beam.

In a certain candidate vascular wall boundary point $b_i(j')$, when a plurality of first evaluation values are calculated, the maximum value among these may be set as the first evaluation value.

Similarly to the above, taking the maximum value at the 30% intensity position of the intensity value selected in a descending order is an example, and the evaluation function which preferably takes the maximum value at a 10% intensity position to an 80% intensity position, and more preferably, at a 20% intensity position to a 70% intensity position may be appropriately determined. The evaluation function may be appropriately changed depending on how to take intensity.

As the first evaluation function, a value obtained by multiplying the intensity of the sound ray signal by a predetermined coefficient and a value obtained by multiplying the amount of change with respect to the depth of the sound ray signal by a predetermined coefficient may be used. For example, when the intensity of the sound ray signal of the depth $b_i(j')$ is $I(b_i(j'))$, the amount of change with respect to the depth is $F(b_i(j'))$, and A1 and A2 are weighting coefficients, the first evaluation function may be set as follows.

$C1(b_i(j'))=A1 \times I(b_i(j')+W)+A2 \times F(b_i(j'))$;

(W is a length of about ½ to ¼ of the wave train length of the transmission wave)

A point $b_i(j')$ in which $C1(b_i(j'))$ is equal to or greater than a predetermined threshold value may be set as a candidate boundary point.

The amount of change with respect to the depth of the intensity (depth direction differential value) $F(b_i(j'))$ may be set as the first evaluation function as follows.

$C1(b_i(j'))=A2 \times F(b_i(j'))$

A point $b_i(j')$ in which $C1(b_i(j'))$ is equal to or greater than a certain threshold value may be set as a candidate boundary point.

In Embodiments 1 and 2 described above, the candidate vascular wall boundary points are determined in the candidate vascular wall boundary point determiner 7, and the first evaluation value is calculated for the determined candidate vascular wall boundary points by the first evaluation value calculator 14 in the boundary determiner 8. However, as shown in FIGS. 16 and 17, the first evaluation value at all depth positions may be calculated based on the first evaluation function in the first evaluation value calculator 114 of the candidate vascular wall boundary point determiner 27 or 37, and points in which the first evaluation value is equal to or greater than a predetermined threshold value may be determined as candidate vascular wall boundary points in the candidate vascular wall boundary point determiner 27 or 37. Since the candidate vascular wall boundary point determiner 27 or 37 has the first evaluation value calculator 114, no first evaluation value calculator is provided in the boundary determiner 18 or 28.

The intima-media boundary position and the media-adventitia boundary position may be temporarily determined using low-resolution sound ray signals, and the periphery of the intima-media boundary position and the media-adventitia boundary position may be searched to determine the candidate vascular wall boundary points.

Low-resolution sound ray signals may be produced at each depth position, instead of taking the average of the sound ray signals in the scan direction, the intensity of the sound ray signals and the amount of change in intensity per unit depth at each depth position may be calculated, the temporary lumen-intima boundary position and the temporary media-adventitia boundary position may be determined based on the amount of change in intensity per unit depth at each depth position, and the search depth range of the candidate lumen-intima boundary points and the search depth range of the candidate media-adventitia boundary points may be respectively determined based on the temporary lumen-intima boundary position and the temporary media-adventitia boundary position.

As the above-described second evaluation value which is similarity between adjacent sound ray signals, for example, SSD (Sum of Squared Difference) or SAD (Sum of Absolute Difference) may be used.

<Method of Calculating all Combinations of Candidate Vascular Wall Boundary Points>

In Embodiment 1 described above, although the calculation amount of combinations of candidate vascular wall boundary points of each line is reduced using the dynamic programming method, all combinations of candidate vascular wall boundary points of each line may be calculated.

For simplification of description, similarly to the description in the dynamic programming method, description will be provided as to a case where the number of lines is ten, the number of sampling points of each line is ten, and all sampling points are selected as candidate vascular wall boundary points. It is assumed that, as the second evaluation value, similarity (correlation) between adjacent sound rays is calculated.

First, the intensity of the first line is used, and $C1(b_i(j))$ of the first evaluation value is calculated at each sampling point of the first line. The first evaluation value is determined for each sampling point.

Next, the intensity of the first line and the second line is used, and $C2(b_1(j),b_2(j'))$ of the second evaluation value is calculated for each sampling point of the second line. That is, since $C2(b_1(j),b_2(j'))$ is calculated corresponding to a sampling point on an adjacent line (in this case, the first line) for each sampling point of the second line, $C2(b_1(j),b_2(j'))$ is calculated in 10×10 combinations.

Next, similarly, $C2(b_2(j),b_3(j'))$ of the second evaluation value is calculated for each sampling point of the third line. That is, since $C2(b_2(j),b_3(j'))$ is calculated corresponding to a sampling point on an adjacent line (in this case, the second line) for each sampling point of the third line, $C2(b_2(j),b_3(j'))$ is calculated in 10×10 combinations.

Similarly, the procedure is sequentially repeated to the tenth line, and finally, $C2(b_9(j),b_{10}(j'))$ of the second evaluation value is calculated for each sampling point of the tenth line.

After the first evaluation value in the sample points on the first line and the second evaluation value in the sample points on the second to tenth lines are calculated, one sampling point is selected for each line, and in combinations of sample points selected in all lines, the sum of the first evaluation value and the second evaluation value is calculated and set as the third evaluation value. Then, a combination of sample points in which the third evaluation value becomes maximum is selected among all combinations, and the combination of sample points is set as a vascular wall boundary point.

Although the first evaluation value is calculated only for the first line, the first evaluation value may be calculated also in the sample points of second to tenth lines, and a combination of sample points in which the third evaluation value becomes maximum may be selected using a value obtained by adding the first evaluation value to the second evaluation value on the second to tenth lines.

As the method of determining the vascular wall boundary point from among the candidate vascular wall boundary points, two methods of a method using the dynamic programming method and a method of examining all combinations have been described. The dynamic programming method has a feature of reducing the calculation amount, and as the number of lines and the number of candidate points increase, the effect relatively increases compared to the method of examining all combinations.

For example, if it is assumed that there are 1 to 10 candidate points in each of ten lines, in the method of examining all combinations, $10^{10}$ calculations are performed.

On the other hand, in the dynamic programming method, since an evaluation function using a correlation coefficient only between a certain line and a line adjacent thereto is utilized and 10×10 combinations are calculated only 10 times, the calculation amount is merely $(10 \times 10) \times 10 = 10^3$. Accordingly, in the method using the dynamic programming method, the calculation amount becomes $1/10^7$ from $10^3/10^{10} = 10^{-7}$ compared to the method of examining all combinations, thereby significantly reducing the calculation amount.

In the above-described Embodiments 1 and 2 and the modification examples thereof, the candidate lumen-intima boundary points are used as the candidate vascular wall boundary points, and the lumen-intima boundary is determined. However, the invention is not limited to the determination of the lumen-intima boundary, and for example, candidate media-adventitia boundary points may be used as the candidate vascular wall boundary points, and a media-adventitia boundary may be determined by the same method as the lumen-intima boundary.

The media-adventitia boundary is determined along with the lumen-intima boundary, whereby it is possible to accurately determine the boundary of the intima-media complex in the ultrasound image, and thus it is possible to measure the intima-media thickness based on the boundary with high precision.

Hereinbefore, although the embodiments of the ultrasound diagnostic apparatus of the invention has been described in detail, the invention is not limited thereto and may be improved or modified in various forms without departing from the gist of the invention.

What is claimed is:

1. An ultrasound diagnostic apparatus, comprising:
   an ultrasound probe which performs transmission and reception of an ultrasonic beam toward a blood vessel in a subject based on an actuation signal and outputs a reception signal of the ultrasonic beam; and
   a diagnostic apparatus body which is connected to the ultrasound probe and performs a processing based on an operation program,
   wherein the diagnostic apparatus body comprises:
      a transmission/reception circuit configured to produce the actuation signal and produce a sound ray signal obtained by processing the reception signal;
      a candidate vascular wall boundary point determining processor configured to determine candidate vascular wall boundary points based on the sound ray signal;
      a first evaluation value calculating processor configured to calculate a first evaluation value representing accuracy of each of the determined candidate vascular wall boundary points as a vascular wall boundary point;
      a second evaluation value calculating processor configured to, by means of a sound ray signal in a predetermined depth range including the determined candidate vascular wall boundary points and a sound ray signal adjacent to the sound ray signal, calculate a second evaluation value representing similarity between the sound ray signal and the adjacent sound ray signal;

a third evaluation value calculating processor configured to calculate a third evaluation value for determining the vascular wall boundary point from among the candidate vascular wall boundary points based on the first evaluation value and the second evaluation value; and a boundary determining processor configured to determine the vascular wall boundary point based on the third evaluation value and determine a vascular wall boundary based on the determined vascular wall boundary point.

2. The ultrasound diagnostic apparatus according to claim 1,
wherein the candidate vascular wall boundary point determining processor includes a temporary boundary position designation processor configured to designate a temporary lumen-intima boundary position and a temporary media-adventitia boundary position for the sound ray signal, and determines a search depth range of the candidate vascular wall boundary points based on the temporary lumen-intima boundary position and the temporary media-adventitia boundary position designated by the temporary boundary position designation processor.

3. The ultrasound diagnostic apparatus according to claim 1,
wherein the candidate vascular wall boundary point determining processor includes an automatic temporary boundary position determining processor configured to automatically determine a temporary lumen-intima boundary position and a temporary media-adventitia boundary position for the sound ray signal, determines the temporary lumen-intima boundary position and the temporary media-adventitia boundary position based on at least one of the intensity and the amount of change of the sound ray signal, and determines a search depth range of the candidate vascular wall boundary points based on the temporary lumen-intima boundary position and the temporary media-adventitia boundary position.

4. The ultrasound diagnostic apparatus according to claim 2,
wherein the candidate vascular wall boundary point determining processor further calculates a maximum point giving the maximum value of the intensity of the sound ray signal within the search depth range,
calculates a shallow portion local maximum point having a local maximum value equal to or greater than a first threshold value at a place shallower than the maximum point and separated from the maximum point more than half the wave train length of a transmission wave at the time of the transmission and reception of the ultrasonic beam within the search depth range,
calculates a first point of interest having intensity of about a second threshold value at a place shallower than the maximum point and within a length of half the wave train length of the transmission wave from the maximum point of the intensity within the search depth range,
calculates a second point of interest having intensity of about a third threshold value at a place shallower than the shallow portion local maximum point and within a length of half the wave train length of the transmission wave from the shallow portion local maximum point within the search depth range, and
determines the first point of interest and the second point of interest as the candidate vascular wall boundary points.

5. The ultrasound diagnostic apparatus according to claim 2,
wherein the first evaluation value calculating processor calculates the first evaluation value based on the distance between the maximum point of the intensity within the search depth range of the sound ray signal and each of the candidate vascular wall boundary points.

6. The ultrasound diagnostic apparatus according to claim 2,
wherein the first evaluation value calculating processor calculates the first evaluation value based on a first evaluation function $C1(b_i(j))$ which takes a maximum value at an intensity position of 10 to 80% of the maximum value of the intensity within the search depth range of the sound ray signal, attenuates as a distance therefrom becomes far and becomes zero at a place separated therefrom by about the wave train length of the transmission wave, and which has a candidate vascular wall boundary position (depth) $b_i(j)$ (where j represents a depth direction position of a candidate vascular wall boundary point) corresponding to the boundary of an intima-media complex of a sound ray $L_i$ (where i represents the position of a sound ray in a scan direction).

7. The ultrasound diagnostic apparatus according to claim 2,
wherein the candidate vascular wall boundary point determining processor determines a plurality of candidate vascular wall boundary points in a descending order of intensity from a maximum point giving the maximum value of the intensity in each sound ray signal within the search depth range, and
the first evaluation value calculating processor calculates, in each of a plurality of the points of interest, at least one shallow portion local maximum point having a local maximum value equal to or greater than a predetermined threshold value at a place shallower than the point of interest and separated from the point of interest more than half the wave train length of the transmission wave at the time of the transmission and reception of the ultrasonic beam within the search depth range, and calculates the first evaluation value based on a first evaluation function which takes a maximum value in at least one shallow portion local maximum point and becomes zero at a place separated therefrom more than the wave train length of the transmission wave.

8. The ultrasound diagnostic apparatus according to claim 1,
wherein, when there are a plurality of first evaluation values, the first evaluation value calculating processor calculates the maximum value of the first evaluation values as the first evaluation value in each of the candidate vascular wall boundary points.

9. An ultrasound diagnostic apparatus, comprising:
an ultrasound probe which performs transmission and reception of an ultrasonic beam toward a blood vessel in a subject and outputs a reception signal of the ultrasonic beam; and a diagnostic apparatus body which is connected to the ultrasound probe and performs a processing based on an operation program, wherein the diagnostic apparatus body comprises:

a transmission/reception circuit configured to produce the actuation signal and produce a sound ray signal obtained by processing the reception signal;

a first evaluation value calculating processor configured to calculate a first evaluation value representing accuracy as a vascular wall boundary of the sound ray signal;

a candidate vascular wall boundary point determining processor configured to determine candidate vascular wall boundary points based on the first evaluation value;

a second evaluation value calculating processor configured to, by means of a sound ray signal in a predetermined depth range including the determined candidate vascular wall boundary points and a sound ray signal adjacent to the sound ray signal, calculate a second evaluation value representing similarly between the sound ray signal and the adjacent sound ray signal;

a third evaluation value calculating processor configured to calculate a third evaluation value for determining the vascular wall boundary point from among the candidate vascular wall boundary points based on the first evaluation value and the second evaluation value; and a boundary determining processor configured to determine the vascular wall boundary point based on the third evaluation value and determine a vascular wall boundary based on the determined vascular wall boundary point.

10. The ultrasound diagnostic apparatus according to claim 9, wherein the candidate vascular wall boundary point determining processor includes a temporary boundary position designation processor configured to designate a temporary lumen-intima boundary position and a temporary media-adventitia boundary position for the sound ray signal, and determines a search depth range of the candidate vascular wall boundary points based on the temporary lumen-intima boundary position and the temporary media-adventitia boundary position designated by the temporary boundary position designation processor.

11. The ultrasound diagnostic apparatus according to claim 9, wherein the candidate vascular wall boundary point determining processor includes an automatic temporary boundary position determining processor configured to automatically determine a temporary lumen-intima boundary position and a temporary media-adventitia boundary position for the sound ray signal, determines the temporary lumen-intima boundary position and the temporary media-adventitia boundary position based on at least one of the intensity and the amount of change of the sound ray signal, and determines a search depth range in the candidate vascular wall boundary points based on the temporary lumen-intima boundary position and the temporary media-adventitia boundary position.

12. The ultrasound diagnostic apparatus according to claim 10, wherein the first evaluation value calculating processor calculates a plurality of points of interest in a descending order of intensity from a maximum point giving the maximum value of the intensity in each sound ray signal within the search depth range, calculates, in each of a plurality of the points of interest, at least one shallow portion local maximum point having a local maximum value equal to or greater than a predetermined threshold value at a place shallower than the point of interest and separated from the point of interest more than half the wave train length of the transmission wave at the time of the transmission and reception of the ultrasonic beam within the search depth range, and calculates the first evaluation value based on a first evaluation function which takes a maximum value in at least one shallow portion local maximum point and becomes zero at a place separated therefrom more than the wave train length of the transmission wave.

13. The ultrasound diagnostic apparatus according to claim 9, wherein, when there are a plurality of first evaluation values, the first evaluation value calculating processor calculates the maximum value of the first evaluation values as the first evaluation value.

14. The ultrasound diagnostic apparatus according to claim 9, wherein the candidate vascular wall boundary point determining processor determines, as the candidate vascular wall boundary points, each point of the sound ray signal in which the first evaluation value is equal to or greater than a predetermined value, or the vicinity of each point of the sound ray signal in which the first evaluation value is equal to or greater than a predetermined value.

15. The ultrasound diagnostic apparatus according to claim 9, wherein the first evaluation value calculating processor sets a first evaluation function by respectively multiplying the intensity of the sound ray signal and the amount of change in intensity of the sound ray signal by a predetermined coefficient and adding the multiplication result, and the candidate vascular wall boundary point determining processor determines, as the candidate vascular wall boundary point, a point in which the first evaluation value calculated by the first evaluation function is equal to or greater than a predetermined value.

16. The ultrasound diagnostic apparatus according to claim 9, wherein the first evaluation value calculating processor sets a first evaluation function by respectively multiplying the amounts of change in intensity of the sound ray signal by a predetermined coefficient and adding the multiplication result, and the candidate vascular wall boundary point determining processor determines, as the candidate vascular wall boundary point, a point in which the first evaluation value calculated by the first evaluation function is equal to or greater than a predetermined value.

17. The ultrasound diagnostic apparatus according to claim 1, wherein the second evaluation value is calculated on the basis of a second evaluation function which represents the deviation of the intensity distribution between one sound ray signal and another sound ray signal different from the sound ray signal.

18. The ultrasound diagnostic apparatus according to claim 1, wherein the second evaluation value is calculated by the following second evaluation function $C2(b_{i-1}(j), b_i(j'))$ using sound ray signals of a plurality of points above and below a candidate vascular wall boundary point including the candidate vascular wall boundary point in a depth direction and sound ray signals adjacent to the sound ray signals;

[Equation 1]
$$C2(b_{i-1}(j), b_i(j')) = \frac{\sum_{k=0}^{WL-1}\left\{f[i-1, j+k] - \left(\sum_{k=0}^{WL-1} f[i-1, j+k]/WL\right)\right\} \left\{f[i, j'+k] - \left(\sum_{k=0}^{WL-1} f[i, j'+k]/WL\right)\right\}}{\sqrt{\sum_{k=0}^{WL-1}\left\{f[i-1, j+k] - \left(\sum_{k=0}^{WL-1} f[i-1, j+k]/WL\right)\right\}^2} \sqrt{\sum_{k=0}^{WL-1}\left\{f[i, j'+k] - \left(\sum_{k=0}^{WL-1} f[i, j'+k]/WL\right)\right\}^2}};$$

$b_i$: a candidate vascular wall boundary position (depth) corresponding to the boundary of an intima-media complex of a sound ray $L_i$, i: the position of a sound ray in a scan direction, j, j': the depth direction positions of the candidate vascular wall boundary points, k: a search depth range, WL: a depth range in which similarity calculation (correlation calculation) is performed (the number of sampling points corresponding to about a wave train length of a transmission wave).

19. The ultrasound diagnostic apparatus according to claim 1,
wherein the second evaluation value is calculated based on a correlation coefficient, a normalized cross-correlation coefficient, the sum of the squares of differences in intensity, or the sum of the absolute values of difference in intensity between sound ray signals of a plurality of points above and below the candidate vascular wall boundary point including the candidate vascular wall boundary point in a depth direction and sound ray signals adjacent to the sound ray signals.

20. The ultrasound diagnostic apparatus according to claim 1,
wherein the third evaluation value is calculated by the following third evaluation function $C_{sum}$ based on the first evaluation value and the second evaluation value;

$$C_{sum} = \sum_{i=1}^{N} C(b_{i-1}(j), b_i(j'));$$ [Equation 2]

$C(b_{i-1}(j), b_i(j')) = W1 C1(b_i(j')) + W2 C2(b_{i-1}(j), b_i(j'));$

W1, W2: a weighting function;
$b_{i-1}(j)$: a candidate vascular wall boundary position (depth) corresponding to the boundary of an intima-media complex of a sound ray $L_{i-1}$; and
$b_i(j')$: a candidate vascular wall boundary position (depth) corresponding to a boundary of an intima-media complex of a sound ray $L_1$.

* * * * *